United States Patent
Boothby

(10) Patent No.: US 12,410,217 B2
(45) Date of Patent: Sep. 9, 2025

(54) PROTEINS FOR STABILIZATION OF BIOLOGICAL MATERIAL

(71) Applicant: UNIVERSITY OF WYOMING, Laramie, WY (US)

(72) Inventor: Thomas Boothby, Laramie, WY (US)

(73) Assignee: UNIVERSITY OF WYOMING, Laramie, WY (US)

( * ) Notice: Subject to any disclaimer, the term of this patent is extended or adjusted under 35 U.S.C. 154(b) by 128 days.

(21) Appl. No.: 17/586,930

(22) Filed: Jan. 28, 2022

(65) Prior Publication Data

US 2023/0054359 A1 Feb. 23, 2023

Related U.S. Application Data

(60) Provisional application No. 63/143,589, filed on Jan. 29, 2021.

(51) Int. Cl.
*C07K 14/435* (2006.01)
*A23B 2/762* (2025.01)
(Continued)

(52) U.S. Cl.
CPC ........ *C07K 14/43504* (2013.01); *A23B 2/762* (2025.01); *A61K 47/42* (2013.01);
(Continued)

(58) Field of Classification Search
CPC .............. C07K 14/43504; G16B 15/20; G16B 15/30; A23L 3/3526; A61K 47/42;
(Continued)

(56) References Cited

U.S. PATENT DOCUMENTS

2021/0087236 A1* 3/2021 Boothby ................ A61K 47/42
2023/0404919 A1* 12/2023 Seydoux .................. A61K 8/06

FOREIGN PATENT DOCUMENTS

WO 2018034867 A1 2/2018

OTHER PUBLICATIONS

Shimizu S, Smith DJ. 2004. Preferential hydration and the exclusion of cosolvents from protein surfaces. J Chem Phys 121:1148-1154.
(Continued)

*Primary Examiner* — Louise W Humphrey
*Assistant Examiner* — Rachel Emily Martin
(74) *Attorney, Agent, or Firm* — Patterson + Sheridan, LLP

(57) ABSTRACT

Embodiments of the present disclosure generally relate to methods and compositions for stabilizing biological material using intrinsically disordered proteins. In an embodiment, a composition is provided, the composition including a first component comprising at least one intrinsically disordered protein; and a second component comprising at least one biological material of interest, at least one biologically-derived material of interest, or both, the second component being free of the at least one intrinsically disordered protein. The methods and compositions include at least one intrinsically disordered protein that can be modified to prevent, or at least mitigate, polymerization thereof and the formation of gel-like matrices, thereby, e.g., improving the ability of the intrinsically disordered proteins to protect and stabilize sensitive biological materials.

18 Claims, 7 Drawing Sheets
(1 of 7 Drawing Sheet(s) Filed in Color)
Specification includes a Sequence Listing.

(51) Int. Cl.
A61K 47/42 (2017.01)
C12N 9/10 (2006.01)
C12N 9/96 (2006.01)
G16B 15/20 (2019.01)
G16B 15/30 (2019.01)

(52) U.S. Cl.
CPC ............ *C12N 9/1025* (2013.01); *C12N 9/96* (2013.01); *C12Y 203/03001* (2013.01); *G16B 15/20* (2019.02); *G16B 15/30* (2019.02); *A23V 2002/00* (2013.01)

(58) Field of Classification Search
CPC .................... C12N 9/1025; C12N 9/96; C12Y 203/03001; A23V 2002/00
See application file for complete search history.

(56) References Cited

OTHER PUBLICATIONS

Tapia H, Koshland DE. 2014. Trehalose is a versatile and long-lived chaperone for desiccation tolerance. Curr Biol 24:2758-2766.
Tapia H, Young L, Fox D, Bertozzi CR, Koshland D. 2015. Increasing intracellular trehalose is sufficient to confer desiccation tolerance to *Saccharomyces cerevisiae*. Proc Natl Acad Sci U S A 112:6122-6127.
Tripathi R. 2012. Functional Characterisation of LEA Proteins from Bdelloid Rotifers.
Tripathi R, Boschetti C, McGee B, Tunnacliffe A. 2012. Trafficking of bdelloid rotifer late embryogenesis abundant proteins. J Exp Biol 215:2786-2794.
Valori A, McDonald PJ, Scrivener KL. 2013. The morphology of C—S—H: Lessons from 1H nuclear magnetic resonance relaxometry. Cement and Concrete Research. doi:10.1016/j.cemconres.2013.03.011.
Van Dijk E, Hoogeveen A, Abeln S. 2015. The hydrophobic temperature dependence of amino acids directly calculated from protein structures. PLoS Comput Biol 11:e1004277.
Wang H, Wang R, Song Y, Kamal T, Lv Y, Zhu B, Tao X, Tan M. 2018. A fast and non-destructive LF-NMR and MRI method to discriminate adulterated shrimp. J Food Meas Charact 12:1340-1349.
Williams AD, Portelius E, Kheterpal I, Guo J-T, Cook KD, Xu Y, Wetzel R. 2004. Mapping abeta amyloid fibril secondary structure using scanning proline mutagenesis. J Mol Biol 335:833-842.
Wolkers WF, McCready S, Brandt WF, Lindsey GG, Hoekstra FA. 2001. Isolation and characterization of a D-7 LEA protein from pollen that stabilizes glasses in vitro. Biochim Biophys Acta 1544:196-206.
Wu C, Biancalana M, Koide S, Shea J-E. 2009. Binding modes of thioflavin-T to the single-layer beta-sheet of the peptide self-assembly mimics. J Mol Biol 394:627-633.
Yamaguchi A, Tanaka S, Yamaguchi S, Kuwahara H, Takamura C, Imajoh-Ohmi S, Horikawa DD, Toyoda A, Katayama T, Arakawa K, Fujiyama A, Kubo T, Kunieda T. 2012. Two novel heat-soluble protein families abundantly expressed in an anhydrobiotic tardigrade. PLoS One 7:e44209.
Yathisha NS, Barbara P, Gügi B, Yogendra K, Jogaiah S, Azeddine D, Sharatchandra RG. 2020. Vegetative desiccation tolerance in : biochemical and physiological responses. Heliyon 6:e04948.
Zheng J-M, Chin W-C, Khijniak E, Khijniak E Jr, Pollack GH. 2006. Surfaces and interfacial water: evidence that hydrophilic surfaces have long-range impact. Adv Colloid Interface Sci 127:19-27.
Zipp A, James TL, Kuntz ID, Shohet SB. 1976. Water proton magnetic resonance studies of normal and sickle erythrocytes Temperature and volume dependence. Biochimica et Biophysica Acta (BBA)—General Subjects. doi:10.1016/0304-4165(76)90037-4.
Antalek B. 2006. Accounting for spin relaxation in quantitative pulse gradient spin echo NMR mixture analysis. J Am Chem Soc 128:8402-8403.
Sakumichi N, Yoshikawa Y, Sakai T. 2021. Linear elasticity of polymer gels in terms of negative energy elasticity. Polym J. doi:10.1038/s41428-021-00529-4.
Sanders DW, Kedersha N, Lee DSW, Strom AR, Drake V, Riback JA, Bracha D, Eeftens JM, Iwanicki A, Wang A, Wei M-T, Whitney G, Lyons SM, Anderson P, Jacobs WM, Ivanov P, Brangwynne CP. 2020. Competing Protein-RNA Interaction Networks Control Multiphase Intracellular Organization. Cell 181:306-324.e28.
Savitsky A, Malferrari M, Francia F, Venturoli G, Möbius K. 2010. Bacterial photosynthetic reaction centers in trehalose glasses: coupling between protein conformational dynamics and electron-transfer kinetics as studied by laser-flash and high-field EPR spectroscopies. J Phys Chem B 114:12729-12743.
Adhikari A, Park W-W, Kwon O-H. 2020. Hydrogen-Bond Dynamics and Energetics of Biological Water. Chempluschem 85:2657-2665.
Ahmed M, Namboodiri V, Singh AK, Mondal JA. 2014. On the intermolecular vibrational coupling, hydrogen bonding, and librational freedom of water in the hydration shell of mono- and bivalent anions. J Chem Phys 141:164708.
Alacik Develioglu I, Ozel B, Sahin S, Oztop MH. 2020. NMR Relaxometry and magnetic resonance imaging as tools to determine the emulsifying characteristics of quince seed powder in emulsions and hydrogels. Int J Biol Macromol 164:2051-2061.
Almdal K, Dyre J, Hvidt S, Kramer O. 1993. Towards a phenomenological definition of the term "gel." Polymer Gels and Networks. doi:10.1016/0966-7822(93)90020-i.
Atta-ur-Rahman, Atta-ur-Rahman, Choudhary MI. 1996. Spin-Echo and Polarization Transfer. Solving Problems with NMR Spectroscopy. doi:10.1016/b978-012066320-0/50004-5.
Barth A. 2007. Infrared spectroscopy of proteins. Biochim Biophys Acta 1767:1073-1101.
Barth A, Zscherp C. 2002. What vibrations tell us about proteins. Q Rev Biophys 35:369-430.
Belton PS, Gil AM. 1994. IR and Raman spectroscopic studies of the interaction of trehalose with hen egg white lysozyme. Biopolymers 34:957-961.
Bevington PR, Bevington RR. 1969. Data Reduction and Error Analysis for the Physical Sciences. McGraw-Hill College.
Biancalana M, Makabe K, Koide A, Koide S. 2009. Molecular mechanism of thioflavin-T binding to the surface of beta-rich peptide self-assemblies. J Mol Biol 385:1052-1063.
Boni LJ, Zurfluh R, Widmer M, Fischer P, Windhab EJ, Rühs PA, Kuster S. 2017. Hagfish slime exudate stabilization and its effect on slime formation and functionality. Biol Open 6:1115-1122.
Boothby TC. 2021. Water content influences the vitrified properties of CAHS proteins. Mol Cell.
Boothby TC. 2019. Mechanisms and evolution of resistance to environmental extremes in animals. Evodevo 10:30.
Boothby TC, Pielak GJ. 2017. Intrinsically Disordered Proteins and Desiccation Tolerance: Elucidating Functional and Mechanistic Underpinnings of Anhydrobiosis. Bioessays 39. doi: 10.1002/bies.201700119.
Boothby TC, Tapia H, Brozena AH, Piszkiewicz S, Smith AE, Giovannini I, Rebecchi L, Pielak GJ, Koshland D, Goldstein B. 2017. Tardigrades Use Intrinsically Disordered Proteins to Survive Desiccation. Mol Cell 65:975-984.e5.
Boothby TC, Tenlen JR, Smith FW, Wang JR, Patanella KA, Nishimura EO, Tintori SC, Li Q, Jones CD, Yandell M, Messina DN, Glasscock J, Goldstein B. 2015. Evidence for extensive horizontal gene transfer from the draft genome of a tardigrade. Proc Natl Acad Sci U S A 112:15976-15981.
Buitink J, Leprince O. 2004. Glass formation in plant anhydrobiotes: survival in the dry state. Cryobiology 48:215-228.
Butler WL. 1970. Higher derivative analysis of complex absorption spectra. Photochem Photobiol 12:439-450.
Chakrabortee S, Tripathi R, Watson M, Schierle GSK, Kurniawan DP, Kaminski CF, Wise MJ, Tunnacliffe A. 2012. Intrinsically disordered proteins as molecular shields. Mol Biosyst 8:210-219.

(56) References Cited

OTHER PUBLICATIONS

Choi J-M, Holehouse AS, Pappu RV. 2020. Physical Principles Underlying the Complex Biology of Intracellular Phase Transitions. Annu Rev Biophys 49:107-133.
Clark AH, Saunderson DH, Suggett A. 1981. Infrared and laser-Raman spectroscopic studies of thermally-induced globular protein gels. Int J Pept Protein Res 17:353-364.
Colby RH. 2010. Structure and linear viscoelasticity of flexible polymer solutions: comparison of polyelectrolyte and neutral polymer solutions. Rheol Acta 49:425-442.
Cordone L, Cottone G, Giuffrida S, Palazzo G, Venturoli G, Viappiani C. 2005. Internal dynamics and protein-matrix coupling in trehalose-coated proteins. Biochim Biophys Acta 1749:252-281.
Crowe JH, Carpenter JF, Crowe LM. 1998. The role of vitrification in anhydrobiosis. Annu Rev Physiol 60:73-103.
Crowe JH, Clegg JS. 1973. Anhydrobiosis. Hutchinson Ross Publishing Company.
Das RK, Pappu RV. 2013. Conformations of intrinsically disordered proteins are influenced by linear sequence distributions of oppositely charged residues. Proc Natl Acad Sci U S A 110:13392-13397.
Denekamp NY, Reinhardt R, Kube M, Lubzens E. 2010. Late embryogenesis abundant (LEA) proteins in nondesiccated, encysted, and diapausing embryos of rotifers. Biol Reprod 82:714-724.
Deshmukh SS, Williams JC, Allen JP, Kálmán L. 2011a. Light-induced conformational changes in photosynthetic reaction centers: dielectric relaxation in the vicinity of the dimer. Biochemistry 50:340-348.
Deshmukh SS, Williams JC, Allen JP, Kálmán L. 2011b. Light-Induced Conformational Changes in Photosynthetic Reaction Centers: Redox-Regulated Proton Pathway near the Dimer. Biochemistry. doi:10.1021/bi200169y.
Dignon GL, Zheng W, Kim YC, Mittal J. 2019. Temperature-Controlled Liquid-Liquid Phase Separation of Disordered Proteins. ACS Cent Sci 5:821-830.
Dill KA, Alonso DOV, Hutchinson K. 1989. Thermal stabilities of globular proteins. Biochemistry. doi: 10.1021/bi00439a019.
Ectors D, Goetz-Neunhoeffer F, Hergeth W-D, Dietrich U, Neubauer J. 2016. In situ 1 H-TD-NMR: Quantification and microstructure development during the early hydration of alite and OPC. Cement and Concrete Research. doi:10.1016/j.cemconres.2015.10.011.
Emenecker RJ, Griffith D, Holehouse AS. 2021. Metapredict: A fast, accurate, and easy-to-use predictor of consensus disorder and structure. bioRxiv. doi:10.1101/2021.05.30.446349.
Emsley JW, Feeney J. 1999. Magnetic Resonance, Historical Perspective. Encyclopedia of Spectroscopy and Spectrometry. doi:10.1006/rwsp.2000.0165.
Erkut C, Penkov S, Khesbak H, Vorkel D, Verbavatz J-M, Fahmy K, Kurzchalia TV. 2011. Trehalose renders the dauer larva of Caenorhabditis elegans resistant to extreme desiccation. Curr Biol 21:1331-1336.
Feher G, Allen JP, Okamura MY, Rees DC. 1989. Structure and function of bacterial photosynthetic reaction centres. Nature 339:111-116.
Fenimore PW, Chen G, Frauenfelder H, McMahon BH, Swenson J, Jansson H, Stroe I, Young RD, Berendzen J. 2009 Coupling of Solvent and Protein Dynamics: Mossbauer and Incoherent Neutron Scattering From Dielectric Relaxation Data. Biophysical Journal. doi:10.1016/j.bpj.2008.12.1622.
Francia F, Dezi M, Mallardi A, Palazzo G, Cordone L, Venturoli G. 2008. Protein-matrix coupling/uncoupling in "dry" systems of photosynthetic reaction center embedded in trehalose/sucrose: the origin of trehalose peculiarity. J Am Chem Soc 130:10240-10246.
Francia F, Malferrari M, Sacquin-Mora S, Venturoli G. 2009. Charge recombination kinetics and protein dynamics in wild type and carotenoid-less bacterial reaction centers: studies in trehalose glasses. J Phys Chem B 113:10389-10398.
Furuki T, Takahashi Y, Hatanaka R, Kikawada T, Furuta T, Sakurai M. 2020. Group 3 LEA Protein Model Peptides Suppress Heat-Induced Lysozyme Aggregation. Elucidation of the Underlying Mechanism Using Coarse-Grained Molecular Simulations. J Phys Chem B 124:2747-2759.

Ge X, Yang Y, Sun Y, Cao W, Ding F. 2018. Islet Amyloid Polypeptide Promotes Amyloid-Beta Aggregation by Binding-Induced Helix-Unfolding of the Amyloidogenic Core. ACS Chem Neurosci 9:967-975.
Ghi PY, Hill DJT, Whittaker AK. 2002. (1)H NMR study of the states of water in equilibrium poly(HEMA-co-THFMA) hydrogels. Biomacromolecules 3:991-997.
Goormaghtigh E, Vigneron L, Scarborough GA, Ruysschaert JM. 1994. Tertiary conformational changes of the Neurospora crassa plasma membrane H(+)-ATPase monitored by hydrogen/deuterium exchange kinetics. A Fourier transformed infrared spectroscopy approach. J Biol Chem 269:27409-27413.
Goormaghtigh, E, de Johgn HJH, Ruysschaert JM. 1996. Relevance of Protein Thin Films Prepared for Attenuated Total Reflection Fourier Transform Infrared Spectroscopy: Significance of the pH. Appl Spectrosc 50:1519-1527.
Goyal K, Walton LJ, Tunnacliffe A. 2005. LEA proteins prevent protein aggregation due to water stress. Biochem J 388:151-157.
Gray KA, Farchaus JW, Wachtveitl J, Breton J, Oesterhelt D. 1990. Initial characterization of site-directed mutants of tyrosine M210 in the reaction centre of Rhodobacter sphaeroides. EMBO J 9:2061-2070.
Greenspan L. 1977. Humidity Fixed Points of Binary Saturated Aqueous Solutions. Journal of Research of the National Bureau of Standards—A Physics and Chemistry 81A:89-96.
Hailwood AJ, Horrobin S. 1946. Absorption of water by polymers: analysis in terms of a simple model. Trans Faraday Soc 42:B084.
Haris PI, Coke M, Chapman D. 1989. Fourier transform infrared spectroscopic investigation of rhodopsin structure and its comparison with bacteriorhodopsin. Biochim Biophys Acta 995:160-167.
Harmon TS, Holehouse AS, Rosen MK, Pappu RV. 2017. Intrinsically disordered linkers determine the interplay between phase separation and gelation in multivalent proteins. Elife 6. doi:10.7554/eLife.30294.
Hatanaka R, Hagiwara-Komoda Y, Furuki T, Kanamori Y, Fujita M, Cornette R, Sakurai M, Okuda T, Kikawada T. 2013. An abundant LEA protein in the anhydrobiotic midge, PvLEA4, acts as a molecular shield by limiting growth of aggregating protein particles. Insect Biochem Mol Biol 43:1055-1067.
Hengherr S, Heyer AG, Köhler H-R, Schill RO. 2008. Trehalose and anhydrobiosis in tardigrades—evidence for divergence in responses to dehydration. FEBS J 275:281-288.
Hengherr S, Worland MR, Reuner A, Brümmer F, Schill RO. 2009. High-temperature tolerance in anhydrobiotic tardigrades is limited by glass transition. Physiol Biochem Zool 82:749-755.
Hesgrove C, Boothby TC. 2020. The biology of tardigrade disordered proteins in extreme stress tolerance. Cell Commun Signal 18:178.
Holehouse AS, Das RK, Ahad JN, Richardson MOG, Pappu RV. 2017. CIDER: Resources to Analyze Sequence-Ensemble Relationships of Intrinsically Disordered Proteins. Biophys J 112:16-21.
Hopkins JB, Gillilan RE, Skou S. 2017. : improvements to a free open-source program for small-angle X-ray scattering data reduction and analysis. J Appl Crystallogr 50:1545-1553.
Ikeda K, Suzuki S, Shigemitsu Y, Tenno T, Goda N, Oshima A, Hiroaki H. 2020. Presence of intrinsically disordered proteins can inhibit the nucleation phase of amyloid fibril formation of A?(1-42) in amino acid sequence independent manner. Scientific Reports. doi:10.1038/s41598-020-69129-1.
Imai K, Mitaku S. 2005. Mechanisms of secondary structure breakers in soluble proteins. Biophysics 1:55-65.
Iwata T, Paddock ML, Okamura MY, Kandori H. 2009. Identification of FTIR bands due to internal water molecules around the quinone binding sites in the reaction center from Rhodobacter sphaeroides. Biochemistry 48:1220-1229.
Käiväräinen AI, Sukhanova G, Goryunov AS. 1984. Changes in water properties in serum albumin solutions induced by alterations in protein flexibility. NMR studies. Folia Biol 30:84-92.
Kesimer M, Makhov AM, Griffith JD, Verdugo P, Sheehan JK. 2010. Unpacking a gel-forming mucin: a view of MUC5B organization after granular release. Am J Physiol Lung Cell Mol Physiol 298:L15-22.

(56) References Cited

OTHER PUBLICATIONS

Klaips CL, Jayaraj GG, Ulrich Hartl F. 2018. Pathways of cellular proteostasis in aging and disease. Journal of Cell Biology. doi:10.1083/jcb.201709072.

Koubaa S, Bremer A, Hincha DK, Brini F. 2019. Structural properties and enzyme stabilization function of the intrinsically disordered LEA_4 protein TdLEA3 from wheat. Sci Rep 9:3720.

Laage D, Elsaesser T, Hynes JT. 2017. Water Dynamics in the Hydration Shells of Biomolecules. Chem Rev 117:10694-10725.

Lapinski J, Tunnacliffe A. 2003. Anhydrobiosis without trehalose in bdelloid rotifers. FEBS Lett 553:387-390.

Larson SB, Day JS, Nguyen C, Cudney R, McPherson A. 2009. Structure of pig heart citrate synthase at 1.78 A resolution. Acta Crystallogr Sect F Struct Biol Cryst Commun 65:430-434.

Laskowska E, Kuczy?ska-Wi?nik D. 2020. New insight into the mechanisms protecting bacteria during desiccation. Curr Genet 66:313-318.

Lerbret A, Affouard F, Hedoux A, Krenzlin S, Siepmann J, Bellissent-Funel M-C, Descamps M. 2012. How strongly does trehalose interact with lysozyme in the solid state? Insights from molecular dynamics simulation and inelastic neutron scattering. J Phys Chem B 116:11103-11116.

Li P, Banjade S, Cheng H-C, Kim S, Chen B, Guo L, Llaguno M, Hollingsworth JV, King DS, Banani SF, Russo PS, Jiang Q-X, Nixon BT, Rosen MK. 2012. Phase transitions in the assembly of multivalent signalling proteins. Nature 483:336-340.

Malferrari M, Francia F, Venturoli G. 2011. Coupling between electron transfer and protein-solvent dynamics: FTIR and laser-flash spectroscopy studies in photosynthetic reaction center films at different hydration levels. J Phys Chem B 115:14732-14750.

Malferrari M, Venturoli G, Francia F, Mezzetti A. 2012. A new method for D2O/H2O exchange in infrared spectroscopy of proteins. Spectroscopy 12:337-342.

Malferrari M, Francia F, Venturoli G. 2015. Retardation of Protein Dynamics by Trehalose in Dehydrated Systems of Photosynthetic Reaction Centers. Insights from Electron Transfer and Thermal Denaturation Kinetics. J Phys Chem B 119:13600-13618.

Malferrari M, Francia F, Mezzetti A, Venturoli G. 2016. Kinetic effects in dehydration, rehydration, and isotopic exchange of bacterial photosynthetic reaction centers. Biomedical Spectroscopy and Imaging 5:185-196.

Malferrari M, Mezzetti A, Francia F, Venturoli G. 2013. Effects of dehydration on light-induced conformational changes in bacterial photosynthetic reaction centers probed by optical and differential FTIR spectroscopy. Biochim Biophys Acta 1827:328-339.

Malferrari M, Savitsky A, Lubitz W, Möbius K, Venturoli G. 2016. Protein Immobilization Capabilities of Sucrose and Trehalose Glasses: The Effect of Protein/Sugar Concentration Unraveled by High-Field EPR. J Phys Chem Lett 7:4871-4877.

Mao AH, Pappu RV. 2012. Crystal lattice properties fully determine short-range interaction parameters for alkali and halide ions. J Chem Phys 137:064104.

Marechal Y. 2011. The molecular structure of liquid water delivered by absorption spectroscopy in the whole IR region completed with thermodynamics data. J Mol Struct 1004:146-155.

Martin EW, Holehouse AS, Grace CR, Hughes A, Pappu RV, Mittag T. 2016. Sequence Determinants of the Conformational Properties of an Intrinsically Disordered Protein Prior to and upon Multisite Phosphorylation. J Am Chem Soc 138:15323-15335.

Martin EW, Holehouse AS, Peran I, Farag M, Incicco JJ, Bremer A, Grace CR, Soranno A, Pappu RV, Mittag T. 2020. Valence and patterning of aromatic residues determine the phase behavior of prion-like domains. Science 367:694-699.

McComb DW, Lengyel J, Barry Carter C. 2019. Cryogenic transmission electron microscopy for materials research. MRS Bulletin. doi:10.1557/mrs.2019.283.

McGibbon RT, Beauchamp KA, Harrigan MP, Klein C, Swails JM, Hernández CX, Schwantes CR, Wang L-P, Lane TJ, Pande VS. 2015. MDTraj: a modern, open library for the analysis of molecular dynamics trajectories. Biophys J 109:1528-1532.

McMahon BH, Muller JD, Wraight CA, Nienhaus GU. 1998. Electron transfer and protein dynamics in the photosynthetic reaction center. Biophys J 74:2567-2587.

Metskas LA, Rhoades E. 2015. Conformation and Dynamics of the Troponin I C-Terminal Domain: Combining Single-Molecule and Computational Approaches for a Disordered Protein Region. J Am Chem Soc 137:11962-11969.

Mitsumasu K, Kanamori Y, Fujita M, Iwata K-I, Tanaka D, Kikuta S, Watanabe M, Cornette R, Okuda T, Kikawada T. 2010. Enzymatic control of anhydrobiosis-related accumulation of trehalose in the sleeping chironomid, Polypedilum vanderplanki. FEBS J 277:4215-4228.

Nabedryk E, Bagley KA, Thibodeau DL, Bauscher M, Mantele W, Breton J. 1990. A protein conformational change associated with the photoreduction of the primary and secondary quinones in the bacterial reaction center. FEBS Lett 266:59-62.

Namioka S, Yoshida N, Konno H, Makabe K. 2020. Residue-Specific Binding Mechanisms of Thioflavin T to a Surface of Flat ?-Sheets within a Peptide Self-Assembly Mimic. Biochemistry 59:2782-2787.

Palazzo G, Mallardi A, Hochkoeppler A, Cordone L, Venturoli G. 2002. Electron transfer kinetics in photosynthetic reaction centers embedded in trehalose glasses: trapping of conformational substates at room temperature. Biophys J 82:558-568.

Pattni V, Vasilevskaya T, Thiel W, Heyden M. 2017. Distinct Protein Hydration Water Species Defined by Spatially Resolved Spectra of Intermolecular Vibrations. J Phys Chem B 121:7431-7442.

Peccati F, Pantaleone S, Riffet V, Solans-Monfort X, Contreras-García J, Guallar V, Sodupe M. 2017. Binding of Thioflavin T and Related Probes to Polymorphic Models of Amyloid-? Fibrils. J Phys Chem B 121:8926-8934.

Piszkiewicz S, Gunn KH, Warmuth O, Propst A, Mehta A, Nguyen KH, Kuhlman E, Guseman AJ, Stadmiller SS, Boothby TC, Neher SB, Pielak GJ. 2019. Protecting activity of desiccated enzymes. Protein Sci 28:941-951.

Popova AV, Rausch S, Hundertmark M, Gibon Y, Hincha DK. 2015. The intrinsically disordered protein LEA7 from *Arabidopsis thaliana* protects the isolated enzyme lactate dehydrogenase and enzymes in a soluble leaf proteome during freezing and drying. Biochim Biophys Acta 1854:1517-1525.

Qiao S, Tian Y, Song P, He K, Song S. 2019. Analysis and detection of decayed blueberry by low field nuclear magnetic resonance and imaging. Postharvest Biol Technol 156:110951.

Rani R. 2019. Lactate Dehydrogenase (LDH): Biochemistry, Function and Clinical Significance.

Raschke TM. 2006. Water structure and interactions with protein surfaces. Curr Opin Struct Biol 16:152-159.

Read JA, Winter VJ, Eszes CM, Sessions RB, Brady RL. 2001. Structural basis for altered activity of M- and H-isozyme forms of human lactate dehydrogenase. Proteins 43:175-185.

Remy A, Gerwert K. 2003. Coupling of light-induced electron transfer to proton uptake in photosynthesis. Nat Struct Biol 10:637-644.

Rondeau-Mouro C, Godfrin C, Cambert M, Rouillac J, Diascorn Y, Lucas T, Grenier D. 2019. Characterization of gluten-free bread crumb baked at atmospheric and reduced pressures using TD-NMR. Magn Reson Chem 57:649-660.

\* cited by examiner

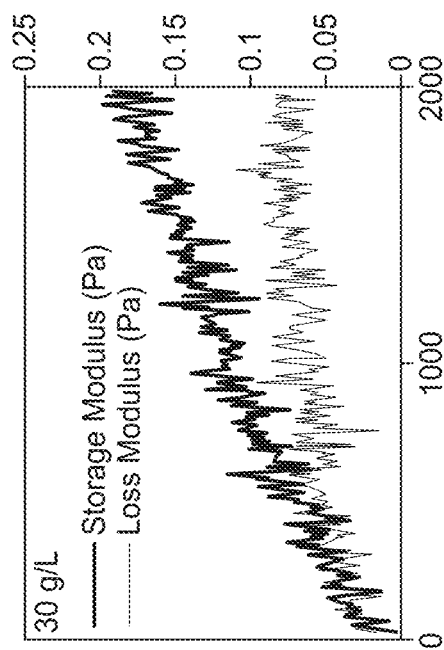
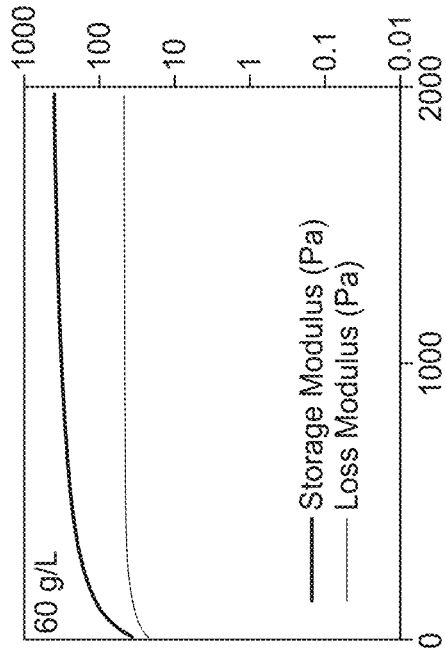
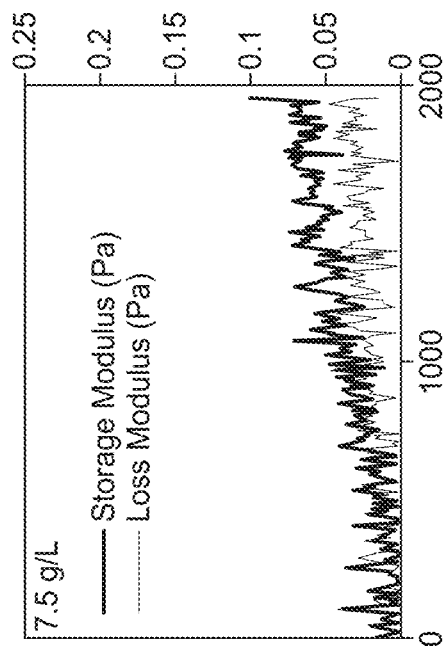
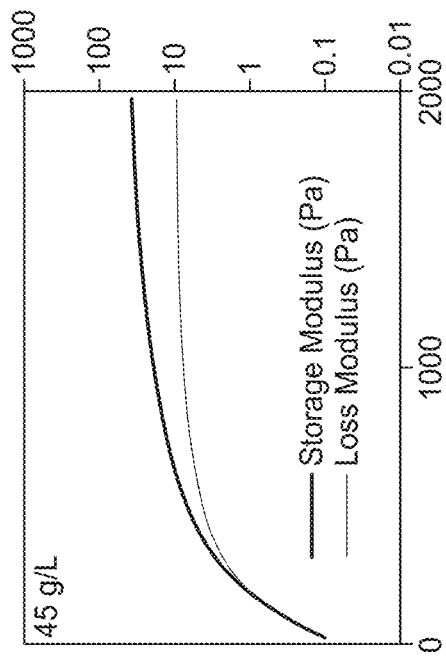

| Schematic | Construct Name | Gelation |
|---|---|---|
|  | WT CAHS D | Gel |
| 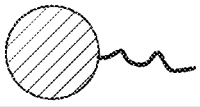 | NL1 | No gel |
|  | CL1 | No gel |
|  | N | No gel |
|  | L | No gel |
|  | C | No gel |
|  | 0.5x Linker | No gel |
FIG. 5

| Protein Variant | | Gelation |
|---|---|---|
| WT CAHS D |  | Gel |
| FL-Proline |  | No gel |
| N-Terminus |  | No gel |
| Linker Region (LR) | 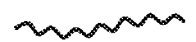 | No gel |
| NLN |  | No gel |
| CLC |  | No gel |
| 2X LR |  | Gel |
| NL2 | 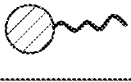 | No gel |
| CL2 |  | No gel |
FIG. 7

PROTEINS FOR STABILIZATION OF BIOLOGICAL MATERIAL

CROSS REFERENCES TO RELATED APPLICATIONS

This application claims priority to U.S. Provisional Patent Application No. 63/143,589, filed Jan. 29, 2021, which is incorporated herein by reference in its entirety.

GOVERNMENT RIGHTS

This invention was made with government support under cooperative agreement W911NF2020137 awarded by the Defense Advanced Research Projects Agency. The government has certain rights in the invention.

REFERENCE TO SEQUENCE LISTING

The material in the accompanying sequence listing is hereby incorporated by reference into this application.

BACKGROUND

Field

Embodiments of the present disclosure generally relate to methods and compositions for stabilizing biological material using intrinsically disordered proteins.

Description of the Related Art

Most biological products derived from living organisms, including vaccines, protein- and nucleic acid-based pharmaceuticals, cosmetic additives, agricultural products, foodstuffs, and the like, are structurally and functionally unstable, thus requiring them to be produced, transported, and stored under certain conditions in order to maintain the integrity thereof. Even under seemingly ideal storage conditions, these biological products generally have limited shelf lives, and under non-ideal conditions, these shelf lives can be limited to hours or even minutes. The increased difficulty in maintaining the integrity of biological products increases the cost to manufacture and deliver the same, resulting in an enormous economic burden.

Numerous molecules are currently used as stabilizing agents to preserve natural products, such as non-reducing sugars, surfactants, salts, amino acids, and the like. However, these additives suffer from many shortcomings, including limited stability in extreme conditions (e.g., freezing and desiccation) and unwanted interactions with the natural products they are meant to preserve. Recently, the extreme stress tolerance mechanisms of living organisms such as tardigrades, plants, rotifers, and bacteria have been studied to develop improved methods for stabilizing sensitive biologically derived products. As a result, these studies have led to the identification and utilization of intrinsically disordered proteins (IDPs) from extremophilic and extremotolerant organisms as stabilizing agents, which provide improved preservation of natural products, especially in extreme conditions. In particular, at least three classes of intrinsically disordered proteins have been identified in tardigrades, and these three classes are collectively known as tardigrade disordered proteins (TDPs). Yet, despite the improved stabilization of biological products over other stabilizing excipients, TDPs are still not without limitations. For example, at concentrations utilized for stabilization, TDPs begin to polymerize and self-associate to form unwanted gel-like substances.

Therefore, there is a need for new and improved methods and compositions for stabilizing biological material using intrinsically disordered proteins.

SUMMARY

Embodiments of the present disclosure generally relate to methods and compositions for stabilizing biological material using intrinsically disordered proteins.

In an embodiment, a composition is provided, the composition including a first component having at least one intrinsically disordered protein; and a second component having at least one biological material of interest, at least one biologically-derived material of interest, or both, the second component being free of the at least one intrinsically disordered protein.

In another embodiment, a method of stabilizing at least one biological material of interest, at least one biologically-derived material of interest, or both is provided. The method includes introducing a first component having at least one intrinsically disordered protein with a second component having the at least one biological material of interest, the at least one biologically-derived material of interest, or both, to form a liquid composition, the second component being free of the at least one intrinsically disordered protein. The liquid composition formed includes the at least one intrinsically disordered protein; and the at least one biological material of interest, the at least one biologically-derived material of interest, or both.

In another embodiment, a recombinant nucleic acid construct is provided, the recombinant nucleic acid construct being selected from the group consisting of: (a) a nucleotide sequence of any one of SEQ ID NOs: 3, 5, 7, 9, 11, 13, 15, 17, 19, 21, 23, 25, 27, 29, 31, or a complement thereof; (b) a nucleotide sequence that encodes a polypeptide comprising an amino acid sequence of any one of SEQ ID NOs: 4, 6, 8, 10, 12, 14, 16, 18, 20, 22, 24, 26, 28, 30, 32, or a complement thereof; (c) a nucleotide sequence having at least about 80%, identity to the nucleotide sequence of any one of (a) or (b); (d) a nucleotide sequence which anneals under stringent hybridization conditions to the nucleotide sequence of any one of (a) to (c), or a complement thereof; (e) a nucleotide sequence that differs from the nucleotide sequences of any one of (a) to (d) above due to the degeneracy of the genetic code; (f) a functional fragment of a nucleotide sequence of any one of (a) to (e); or (g) any combination of the nucleotide sequences of (a)-(f).

BRIEF DESCRIPTION OF THE DRAWINGS

This patent or application file contains at least one drawing executed in color. Copies of this patent or patent application publication with color drawing(s) will be provided by the Office upon request and payment of the necessary fee.

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limited of its scope, and may admit to other equally effective embodiments.

FIG. 1A shows exemplary cone-plate rheological analysis data for the gelation of a cytoplasmic abundant heat soluble (CAHS) protein according to at least one embodiment of the present disclosure.

FIG. 1B shows exemplary cone-plate rheological analysis data for the gelation of a cytoplasmic abundant heat soluble (CAHS) protein according to at least one embodiment of the present disclosure.

FIG. 1C shows exemplary cone-plate rheological analysis data for the gelation of a cytoplasmic abundant heat soluble (CAHS) protein according to at least one embodiment of the present disclosure.

FIG. 1D shows exemplary cone-plate rheological analysis data for the gelation of a cytoplasmic abundant heat soluble (CAHS) protein according to at least one embodiment of the present disclosure.

FIG. 5 shows illustrations of example mutant CAHS D protein constructs and the gel propensity of each example construct according to at least one embodiment of the present disclosure.

FIG. 7 shows illustrations of example mutant CAHS D protein constructs and the gel propensity of each example construct according to at least one embodiment of the present disclosure.

DETAILED DESCRIPTION

Figure 2A:
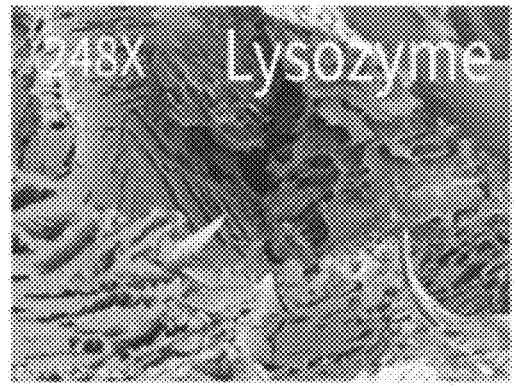
FIG. 2A is a scanning electron microscope (SEM) image of a lysozyme at 248× magnification according to at least one embodiment of the present disclosure.

Embodiments of the present disclosure generally relate to methods and compositions for stabilizing biological material using intrinsically disordered proteins. Briefly, and in some embodiments, the compositions generally include at least one intrinsically disordered protein, and at least one biological material. The methods, in some embodiments, generally include forming such compositions and stabilizing biological material. As described herein, the inventor has found that the use of an intrinsically disordered protein serves to, e.g., stabilize, protect, and/or preserve the biological material. As further described below, the biological material extends to a wide array of materials such as such as polypeptides, nucleotides, lipids, and biologically-derived materials and products such as vaccines, food, pharmaceuticals, biologics, et cetera. In addition, and in some embodiments, the methods and compositions described herein include utilization of a modified intrinsically disordered protein. Such intrinsically disordered proteins are modified to, e.g., prevent or at least mitigation of intra- or inter-polymerization and the formation of gel-like matrices. The inventor found that such modifications can improve the ability of the intrinsically disordered proteins to, e.g., stabilize, protect, and/or preserve sensitive biological materials.

Both biological materials and biologically-derived materials and products such as polypeptides, antibodies, vaccines, food, et cetera, are very sensitive to the environment, being prone to break down outside of ideal storage conditions. Conventionally, in order to maintain stability and activity, certain biological material and biologically-derived materials/products are maintained at cold temperatures (e.g., below 4° C. or below ~20° C.) or ultra-cold temperatures (e.g., less than ~80° C.). Such storage methods represent a large economic and logistical burden, particularly in areas with low access to electricity. Moreover, some biological materials such as protein-based pharmaceuticals are conventionally lyophilized for storage at room temperature. However, the proteins denature as a result of the drying or freezing process. Additives such as non-reducing sugars and surfactants are also conventionally for stabilizing biological material; however, sugars are prone to crystallize, phase separate, or hydrolyze surfactants that can produce peroxides that oxidize sensitive moieties of biological material.

To solve these and other challenges, the inventor has found that intrinsically disordered proteins, such as those possessed by tardigrades, can be used to stabilize biological materials under conditions outside of conventional storage methods and/or use of conventional agents such as non-reducing sugars. That is, biological material can be stabilized via the use of intrinsically disordered proteins and stored at temperatures or conditions outside of the biological material's normal or conventional storage temperatures and conditions. For example, and in some embodiments, the compositions described herein enable, e.g., stabilization of biological material under extreme drought conditions, desiccating conditions, or near-complete water loss, and/or up to about 100° C. via the use of intrinsically disordered proteins. When the biological material is ready to be used, a fluid such as water or buffer solution can be added to the biological material.

Tardigrades, also known as water bears, make up a phylum of small but extremely hardy animals and have the ability to survive extreme stresses, including desiccation. These desiccation-tolerant organisms possess several stress-tolerant intrinsically disordered proteins such as cytoplasmic abundant heat soluble proteins, also known as cytosolic abundant heat soluble proteins, or CAHS proteins. As shown herein, in an effort to develop improved methods and compositions for stabilizing biological material, various tardigrade disordered proteins (TDPs) and modified TDPs have been investigated and their impacts on the stabilization and preservation of biological materials are described. In particular, the inventor has determined that tardigrade CAHS proteins, which enable tardigrades to survive desiccation, are effective protectants of biological material in the dry state as compared to more common, FDA-approved excipients such as trehalose and albumen.

The inventor has also found that the protection and stabilization of biological material via the use of CAHS proteins can be concentration dependent, with higher concentrations of CAHS proteins providing greater protection and stabilization. However, at high concentrations, CAHS proteins have a propensity to self-associate and form gel-like substances. Due to this propensity of CAHS proteins to form unwanted gels, it is desirable to disrupt or modify CAHS proteins in order to prevent polymerization thereof and the formation of gels. Accordingly, such modifications increase the ability of the CAHS proteins to protect and stabilize sensitive biological materials.

Accordingly, and in some embodiments, novel constructs of CAHS proteins having specific mutations and/or modifications that prevent the CAHS proteins from self-assembling and forming gels are described. These modified or mutant CAHS proteins can provide improved ability to protect and stabilize sensitive biological material, especially under extreme conditions such as high temperature, freezing, and/or desiccation. Embodiments of the present disclosure further provide methods for forming these novel constructs, as well as methods for preparing solid or liquid compositions for stabilizing a biological material of interest with these novel constructs.

Embodiments of the present disclosure generally relate to compositions that include at least one intrinsically disordered protein (IDP) and at least one biological material and/or a biologically-derived material. As discussed above, most biological materials and products derived from biological materials (e.g., vaccines, protein and nucleic acid based pharmaceuticals, cosmetics, food, et cetera) must be produced and stored under certain conditions in order to maintain integrity. Even under seemingly ideal storage conditions, the biological material has a limited shelf-life, and under non-ideal conditions, the shelf-life of the biological material can be limited to minutes or hours. Because of the biological material's fragility, the loss of, e.g., food, agricultural products, and biologically-derived pharmaceuticals presents an enormous economic and logistical burden. The inventors have found that, e.g., an intrinsically disordered protein can be utilized to stabilize the biological material under, e.g., non-ideal conditions.

Generally, the compositions described herein include at least two components. The first component includes the at least one intrinsically disordered protein (IDP) and the second component includes the at least one biological material and/or the biologically-derived material. The second component is free of the at least one intrinsically disordered protein. Free of the at least one intrinsically disordered protein means that the second component (e.g., the biological material) is not the at least one IDP. The compositions can be in the form of a solid composition, liquid composition, and/or other compositions as described below.

The at least one IDP of the first component can be a naturally occurring or non-naturally occurring protein. In some examples, the intrinsically disordered protein can be produced by organisms known as tardigrades. The tardigrade-produced intrinsically disordered proteins are referred to herein as tardigrade disordered proteins (TDPs). If desired, the TDPs can be modified or mutated to, e.g., eliminate or at least mitigate a TDP's propensity to polymerize and gel. As discussed herein, such mutated or modified TDPs can be less prone to polymerization and can have an improved ability to protect and stabilize the biological material.

In some embodiments, the at least one IDP of the first component can be, or include, an IDP (e.g., wild-type IDP), a modified/mutant IDP, a TDP (e.g., wild-type TDP), a modified/mutant TDP, or combinations thereof. In some examples, and as further discussed below, the at least one IDP Includes a CAHS protein and/or a modified CAHS protein.

The second component of the compositions described herein includes at least one biological material and/or at least one biologically-derived material. The biological material and/or a biologically-derived material can be derived from a living organism, in its natural state or its modified state, and/or synthesized. The biological material, also referred to as a biological material of interest, can be, or include, any suitable biological material such as at least one or more of the following: a peptide, a polypeptide, a protein, an enzyme, an antibody, a globular protein, a hormone, a nucleic acid, a nucleotide, a lipid, a polylipid, a fat, a monosaccharide, a polysaccharide, a carbohydrate, a cell, a tissue, an organ, a natural product, a derivative thereof, or combinations thereof. The biologically-derived material, also referred to as a biologically-derived product or a biologically-derived material of interest, includes materials that are, e.g., derived from or produced from a biological material, as well as biological materials that have been modified. Such biologically derived materials can include, e.g., a biologic, a vaccine, a cosmetic, a food, an agricultural product, therapeutic agent, a diagnostic agent, an agent used for research purposes, a pharmaceutical such as a protein-based pharmaceutical and/or a nucleic acid-based pharmaceutical, a derivative thereof, and combinations thereof, among others. The inventor contemplates that certain examples of biological materials and biologically-derived materials may fall within or outside both categories; however, such biological materials and biologically-derived materials can be included in the compositions described herein.

Other illustrative, but non-limiting, examples of biological material and/or biologically-derived material can include a nucleic acid-based biologics, nucleic acid-based therapeutics, and nucleic acid-based diagnostics (e.g., a nucleic acid-based gene therapy, a nucleic acid-based vaccine such as an mRNA vaccine, et cetera); lipid-based biologics, lipid-based biologics therapeutics, and lipid-based diagnostics (e.g., lipid-based nanoparticle and lipid-based carrier systems, et cetera); protein-based biologics, protein-based therapeutics, and protein-based diagnostics (e.g., vaccines, antibodies, enzymes, et cetera). The biological material and/or biologically-derived material can be a cosmetic additive and/or an agricultural product. Other biological materials and/or biologically-derived materials are contemplated. The at least one biological material and/or at least one biologically-derived material of the second component can include one or more of the aforementioned materials.

For purposes of the present disclosure, and unless the context indicates otherwise, the terms "biological material," "biological material of interest," biologically-derived material," "biologically-derived product," and "biologically-derived material of interest" are used interchangeably such that reference to one includes reference to the other. For example, reference to "biological material" includes reference to "biological material," "biological material of interest," biologically-derived material," "biologically-derived product," and "biologically-derived material of interest."

The at least one biological material can be heterologous to the IDP. For example, a heterologous polypeptide refers to a non-IDP polypeptide, a non-tardigrade polypeptide, or a polypeptide that is heterologous to the organism, to the genus or to the species from which the particular IDP or TDP is derived. A heterologous cell; tissue or organ as used herein, refers to a cell, tissue or organ that is heterologous to the organism, to the genus, or to the species that naturally produces the particular IDP or TDP.

As described above, the at least one biological material can be an antibody. The antibody can be any suitable type of immunoglobulin, such as IgA, IgD, IgE, IgG, and IgM. The antibody can be monoclonal or polyclonal and can be of any species of origin, including, e.g., camel, goat, human, mouse, rat, rabbit, horse, sheep, or can be a chimeric antibody. The antibody can be a recombinant monoclonal antibody. The antibody can also be chemically constructed. The antibody can also be an antibody fragment, e.g., Fab, Fab', F(ab')$_2$, and/or Fv fragments; domain antibodies; diabodies; vaccibodies; linear antibodies; single-chain antibody molecules; and/or multi-specific antibodies formed from antibody fragments. Also included are antibodies which are altered or mutated for compatibility with species other than the species in which the antibody was produced. For example, antibodies can be humanized or camelized. Humanized forms of non-human (e.g., murine) antibodies are chimeric immunoglobulins, immunoglobulin chains, or fragments thereof (such as Fab, Fab', F(ab')$_2$, Fv, and/or other antigen-binding subsequences or portions of antibodies) which can contain minimal sequence derived from non-human immunoglobulin.

The at least one biological material can be in a purified form or it can be in a mixture (unpurified or partially purified). For example, the at least one biological material can be obtained from, e.g., an organism (animals, bacteria, fungi, plants), the cells of an organism (either cultured or isolated), from serum, and/or from in vitro expression systems, that can then be purified, partially purified, or unpurified. The at least one biological material so produced can then be protected (stabilized) by contact with at least one IDP immediately without any further isolation or purification, or the at least one biological material can be contacted with at least one IDP after the at least one biological material is purified or partially purified. Thus, a mixture can include, e.g., cell culture, serum, and/or one or more constituents of an organism or cell thereof, and/or an in vitro expression system, and the like.

Food includes any suitable food or supplement including, but not limited to, animal-based food, plant-based food, fungi-based food, and the like. Synthetic foods are also contemplated. For example, the food can include a protein-based food such as meat, seafood, a food comprised of plant-based proteins, fungal based proteins, synthetic and lab-grown protein-based food, and the like. As another example, the food can include a carbohydrate-based food such as a plant-based carbohydrate, among others. The food can include a lipid-based food or supplement. Accordingly, and in some embodiments, the at least one IDP can be utilized as a food additive to stabilize a food or food product.

Some embodiments of the at least one IDP are discussed above. The compositions described herein can include any number or combination of IDPs, e.g., TDPs from various tardigrade genera or species. Accordingly, and in some embodiments, the compositions described herein can comprise, consist essentially of, or consist of at least about 1, 2, 3, 4, 5, 6, 7, 8, 9, 10, 11, 12, 13, 14, 15, 16, 17, 18, 19, or 20 or more different IDPs and/or other IDPs (e.g., about 1 to about 25, about 1 to about 20, about 1 to about 15, about 1 to about 10, about 1 to about 5, about 2 to about 10, about 2 to about 5, about 4 to about 10, about 6 to about 10 different IDPs and/or other IDPs). When a composition described herein includes two or more IDPs, the IDPs can be from the same or from any combination of different species or genera. For example, when a composition described herein includes two or more IDPs, the IDPs can be from the same species or genera or from any suitable combination of different species or genera.

Illustrative, but non-limiting, tardigrade genera from which the at least one TDP can be obtained include *Macrobiotus* spp., *Isohypsibius* spp., *Diphascon* spp., *Echiniscus* spp., *Minibiotus* spp., *Doryphoribius* spp., *Paramacrobiotus* spp., *Hypsibius* spp., *Milnesium* spp., *Pseudechiniscus* spp., *Ramazzottius* spp., *Batillipes* spp., *Bryodelphax* spp., *Dactylobiotus* spp., *Echiniscoides* spp., *Calcarobiotus* spp., *Tenuibiotus* spp., *Itaquascon* spp., *Cornecchiniscus* spp., *Halechiniscus* spp., or combinations thereof. In some embodiments, the at least one TDP can be obtained from the tardigrade genera of *Hypsibius* spp., *Paramacrobiotus* spp., *Milnesium* spp. *Ramazzottius* spp., *or combinations thereof. Any suitable number or combination of TDPs from any tardigrade genus or species can be used.*

Illustrative, but non-limiting, tardigrade species from which the at least one TDP can be obtained include *Hypsibius dujardini, Paramacrobiotus richters, Milnesium tardigradum, Ramazzottius varieornatus*, or combinations thereof. Other tardigrade species are contemplated.

The at least one IDP can include a tardigrade disordered protein or polypeptide (which can be isolated) comprising, consisting essentially of, or consisting of:
(a) an amino acid sequence of any one of SEQ ID NOs: 4, 6, 8, 10, 12, 14, 16, 18, 20, 22, 24, 26, 28, 30, 32, or a complement thereof;
(b) an amino acid sequence encoded by a nucleotide sequence of any one of SEQ ID NOs: 3, 5, 7, 9, 11, 13, 15, 17, 19, 21, 23, 25, 27, 29, 31, or a complement thereof;
(c) an amino acid sequence having at least about 50%, at least about 60%, at least about 70%, at least about 80%, at least about 90%, or at least about 95% identity to any one of SEQ ID NOs: 4, 6, 8, 10, 12, 14, 16, 18, 20, 22, 24, 26, 28, 30, 32, or a complement thereof;
(d) an amino acid sequence encoded by a nucleotide sequence having at least about 50%, at least about 60%, al least about 70%, at least about 80%, at least about 90%, or at least about 95% identity to any of SEQ ID NOs: 3, 5, 7, 9, 11, 13, 15, 17, 19, 21, 23, 25, 27, 29, 31, or a complement thereof; and/or
(e) a functional fragment of any one of (a) to (d).

Polypeptides and fragments thereof can be modified for use by the addition, at the amino- and/or carboxyl-terminal ends, of a blocking agent. Such blocking agents can include, e.g., additional related or unrelated peptide sequences that'can be attached to the amino and/or carboxyl terminal residues of the peptide to be administered. For example, one or more non-naturally occurring amino acids, such as D-alanine, can be added to the termini. Alternatively, blocking agents such as pyroglutamic acid or other molecules known in the art can be attached to the amino and/or carboxyl terminal residues, or the amino group at the amino terminus or carboxyl group at the carboxyl terminus can be replaced with a different moiety. Additionally, the peptide terminus can be modified, e.g., by acetylation of the N-terminus and/or amidation of the C-terminus. Likewise, the peptides can be covalently or noncovalently coupled to pharmaceutically acceptable "carrier" proteins prior to use.

Additionally provided herein is a recombinant nucleic acid construct comprising, consisting essentially of, or consisting of:
(a) a nucleotide sequence of any one of SEQ ID NOs: 3, 5, 7, 9, 11, 13, 15, 17, 19, 21, 23, 25, 27, 29, 31, or a complement thereof;
(b) a nucleotide sequence that encodes a polypeptide comprising an amino acid sequence of any one of SEQ ID NOs: 4, 6, 8, 10, 12, 14, 16, 18, 20, 22, 24, 26, 28, 30, 32, or a complement thereof;

(c) a nucleotide sequence having at least about 50%, at least about 60%, at least about 70%, at least about 80%, at least about 90%, or at least about 95% identity to the nucleotide sequence of any one of (a) or (b);
(d) a nucleotide sequence which anneals under stringent hybridization conditions to the nucleotide sequence of any one of (a) to (c), or a complement thereof;
(e) a nucleotide sequence that differs from the nucleotide sequences of any one of (a) to (d) above due to the degeneracy of the genetic code;
(f) a functional fragment of a nucleotide sequence of any one of (a) to (e); or
(g) any combination of the nucleotide sequences of (a)-(f).

In some embodiments, the nucleic acid, nucleotide sequence, or polynucleotide described herein can be a complement (which can be either a full complement or a partial complement) of a nucleic acid, nucleotide sequence, or polynucleotide of the present disclosure. Two nucleotide sequences can be considered to be substantially complementary when the two sequences hybridize to each other under stringent conditions. In some embodiments, two nucleotide sequences considered to be substantially complementary hybridize to each other under highly stringent conditions. Stringent conditions refers to a melting temperature above 65° C., indicating the strength of the hybridization.

In some embodiments, the nucleotide sequences and/or recombinant nucleic acid molecules of the present disclosure can be operatively linked and/or associated with a variety of promoters for expression in cells. Thus, in some embodiments, a recombinant nucleic acid described herein can further include one or more promoters operably linked to one or more nucleotide sequences.

The recombinant nucleic acid molecule can be an expression cassette or can be included within an expression cassette. As used herein, "expression cassette" refers to a recombinant nucleic acid molecule comprising a nucleotide sequence of interest (e.g., a nucleotide sequence encoding an amino acid sequence having at least about 50%, at least about 60%, at least about 70%, at least about 80%, at least about 90%, or at least about 95% identity to of any of SEQ ID NOs: 4, 6, 8, 10, 12, 14, 16, 18, 20, 22, 24, 26, 28, 30, 32, or a complement thereof; and/or a nucleotide sequence having at least about 50%, at least about 60%, at least about 70%, at least about 80%, about at least 90%, or at least about 95% identity to any of SEQ ID NOs: 3, 5, 7, 9, 11, 13, 15, 17, 19, 21, 23, 25, 27, 29, 31, or a complement thereof), wherein said nucleotide sequence can be operably associated with at least a control sequence (e.g., a promoter). Accordingly, some embodiments of the present disclosure provide expression cassettes designed to express the nucleotide sequences described herein in a cell.

An expression cassette comprising a nucleotide sequence can be chimeric, meaning that at least one of its components is heterologous with respect to at least one of its other components. An expression cassette can also be one that is naturally occurring but has been obtained in a recombinant form useful for heterologous expression. An expression cassette also can optionally include a transcriptional and/or translational termination region (i.e., termination region) that is functional in the cell in which the nucleotide sequence of interest is to be expressed.

A variety of transcriptional terminators are available for use in expression cassettes and are responsible for the termination of transcription beyond the heterologous nucleotide sequence of interest and correct mRNA polyadenylation. The termination region can be native to the transcriptional initiation region, can be native to the operably linked nucleotide sequence of interest, can be native to the host organism, or can be derived from another source (i.e., foreign or heterologous to the promoter, the nucleotide sequence of interest, the host organism, or any combination thereof). In addition, and in some embodiments, a coding sequence's native transcription terminator can be used.

An expression cassette can include a nucleotide sequence for a selectable marker, which can be used to select a transformed organism and/or cell. As used herein, "selectable marker" refers to a nucleotide sequence that when expressed imparts a distinct phenotype to the transformed organism or cell expressing the marker and thus allows such transformed organisms or cells to be distinguished from those that do not have the marker. Such a nucleotide sequence can encode either a selectable or screenable marker, depending on whether the marker confers a trait that can be selected for by chemical means, such as by using a selective agent (e.g., an antibiotic, herbicide, or the like), or on whether the marker is simply a trait that one can identify through observation or testing, such as by screening. Of course, many examples of suitable selectable markers useful in various organisms are known in the art and can be used in the expression cassettes described herein.

In addition to expression cassettes, the nucleic acid molecules and nucleotide sequences described herein can be used in connection with vectors. The term "vector" refers to a composition for transferring, delivering or introducing a nucleic acid (or nucleic acids) into a cell. A vector includes a nucleic acid molecule comprising the nucleotide sequence(s) to be transferred, delivered, and/or introduced. Vectors for use in transformation of animals, plants, and other organisms are well known in the art. Illustrative, but non-limiting, examples of general classes of vectors include a viral vector, a plasmid vector, a phage vector, a phagemid vector, a cosmid vector, a fosmid vector, a bacteriophage, an artificial chromosome, or an agrobacterium binary vector in double or single stranded linear or circular form which may or may not be self-transmissible or mobilizable. A vector can transform prokaryotic or eukaryotic host either by integration into the cellular genome or exist extrachromosomally (e.g., an autonomous replicating plasmid with an origin of replication). Additionally included are shuttle vectors by which is meant a DNA vehicle capable, naturally or by design, of replication in two different host organisms, which can be selected from prokaryotic and eukaryotic organisms. In some embodiments, the nucleic acid in the vector is under the control of, and operably linked to, an appropriate promoter or other regulatory elements for transcription in a host cell such as a microbial, e.g. bacterial, or an animal or a plant cell. The vector can be a bi-functional expression vector which functions in multiple hosts. In the case of genomic DNA, this can contain its own promoter or other regulatory elements and in the case of cDNA this can be under the control of an appropriate promoter or other regulatory elements for expression in the host cell.

In some embodiments, the at least one IDP includes one or more wild type IDPs such as one or more wild type CAHS proteins. In some embodiments, the at least one IDP includes one or more modified or mutant TDPs, such as a modified or mutant CAHS protein, such as a modified or mutant CAHS D protein. As described herein, the inventor has found that CAHS proteins can enable tardigrades to survive desiccation and can be effective protectants of biological material in the dry state, outcompeting well known excipients. CAHS proteins, such as CAHS D proteins, is a highly charged 227-residue disordered protein. During its expression and purification, CAHS D proteins undergo a sol-gel phase transition, transitioning from a liquid into a solid gel state. Protection via CAHS D proteins can be concentration dependent, with higher concentrations providing greater protection. However, CAHS D proteins can have an increased propensity to form gels at high concentration. Modifications to, and/or mutations of, CAHS proteins can make such proteins less prone to polymerization and have an improved ability to protect and stabilize the biological material.

Wild type CAHS D proteins have an N-terminus, a C-terminus, and a linker region connecting the two termini. Modified or mutant CAHS D proteins that can be utilized as at least a portion of the at least one IDP of the compositions described herein include:
- (a) a CAHS D protein construct missing at least a portion of the C-terminus;
- (b) a CAHS D protein construct missing at least a portion of the N-terminus;
- (c) a CAHS D protein construct missing at least a portion of the linker region;
- (d) a CAHS D protein construct having only the C-terminus;
- (e) a CAHS D protein construct having only the N-terminus;
- (f) a CAHS D protein construct having only a linker region;
- (g) a CAHS D protein construct having a shorter or larger linker region (e.g., 0.5× linker as the wild type CAHS D protein, or 2× linker as the wild type CAHS D protein or other shorter or larger linker regions);
- (h) a CAHS D protein construct having two N-termini connected by at least a portion of the linker region;
- (i) a CAHS D protein construct having two C-termini connected by at least a portion of the linker region;
- (j) derivatives thereof; and/or
- (k) combinations thereof.

In some embodiments, the at least one IDP comprises a gelling IDP, a non-gelling IDP, or a combination thereof. In some embodiments, the at least one IDP (e.g., a mutant TDP, such as a mutant CAHS D protein construct) provides a level of protective capacity to the at least one biological material. The level of protective capacity is measured by the molarity of IDP at which 50% activity of the citrate synthase enzyme is preserved as described in the Examples (molarity of IDP at which 50% activity is preserved). The molarity of IDP at which 50% activity is preserved can be about 1 mM or less, such as about 0.5 mM or less, such as about 0.25 mM or less, such as about 0.15 mM or less, such as about 0.1 mM or less, such as about 0.08 mM or less, such as about 0.05 mM or less, though other amounts are contemplated.

The composition comprising the at least one IDP and the at least one biological material can be in the form of a liquid (e.g., a solution, a suspension, et cetera) a solid (e.g., powder, particles, et cetera), other compositions, or combinations thereof. The compositions can be stored under ideal conditions or non-ideal conditions. For example, when the biological material is intended to be stored at an ideal temperature of 4° C. according to conventional methods, the compositions described herein comprising the IDP and the biological material can be stored at this ideal temperature or a non-ideal temperature (e.g., greater than about 4° C. or less than about 4° C.). In some embodiments, when dried (e.g., as a solid composition) or when in solution (e.g., as a liquid composition), the biological material can be stabilized over a range of temperatures from about −80° C. to about 100° C., though other temperatures are contemplated. In at least one embodiment, when dried (e.g., as a solid composition) or when in solution (e.g., as a liquid composition), the biological material can be stabilized over a range of temperatures from about −80° C. to about 40° C., though other temperatures are contemplated.

As used herein, "stabilizing" a biological material refers to maintaining the structure and/or the function of the biological material under either aqueous conditions or dried conditions, or after being frozen and/or dried and then thawed and/or rehydrated. In some embodiments, the biological material can be stable at a temperature from about −80° C. to about 100° C. once the at least one biological material is introduced or contacted with the at least one IDP. In some embodiments, at least about 10% to about 100% (e.g., about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100%, or any range or value therein) of the structure and function of the stabilized biological material is maintained. Thus, in some embodiments, about 10% to about 90%, about 10 to about 85% about 10% to about 80%, about 10% to about 75%, about 10% to about 70%, about 10% to about 60%, about 10% to about 50%, about 20% to about 90%, about 20% to about 85%, about 20% to about 80%, about 20% to about 75%, about 20% to about 70%, about 20% to about 60%, about 20% to about 50%, about 30% to about 90%, about 30 to about 85%, about 30% to about 80%, about 30% to about 75%, about 30% to about 70%, about 30% to about 60%, about 30% to about 50%, about 40% to about 90%, about 40 to about 85%, about 40% to about 80%, about 40% to about 75%, about 40% to about 70%, about 40% to about 60%, about 40% to about 50%, about 50% to about 90%, about 50 to about 85%, about 50% to about 80%, about 50% to about 75%, about 50% to about 70%, about 50% to about 60%, and the like, of the structure and function of the biological material is maintained.

In some embodiments, a liquid composition is provided comprising, consisting essentially of, or consisting of: at least one IDP; and at least one biological material. The at least one IDP and/or the at least one biological material can each, independently, exist as one or more ions in, e.g., solution or suspension.

In some embodiments, a solid composition is provided comprising, consisting essentially of, or consisting of: at least one IDP; and at least one biological material (e.g., biological material, biological material of interest, biologically-derived material, or biologically-derived material of interest). In some embodiments, a solid composition can be produced by drying or partially drying a liquid composition. In some embodiments, a solid composition of the present disclosure can include about 0% to about 5% water (e.g., about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5% water, or any range or value therein), though other amounts of water are contemplated. As used herein, "partially drying" refers to drying a composition or solution such that it comprises less water than when the drying process began. Thus, for example, "partially drying" can refer to removing about 5% to about 90% of the water that was present in the composition or solution prior to initiating the drying process. (e.g., about 5%, 10%, 15%, 20%, 25%, 30%, 35%, 40%), 45%, 50%, 55%, 60%, 65%, 70%, 75%, 80%, 85%, or 90% (or any range or value therein), though other amounts of water are contemplated. Thus, and in some embodiments, the amount of water removed when a composition or solution is partially dried can be from about 10% to about 90%, about 20% to about 90%, about 30% to about 90%, about 40% to about 90%, about 50% to about 90%, about 60% to about 90%, about 10% to about 80%, about 20% to about 80%, about 30% to about 80%, about 40% to about 80%, about 50% to about 80%, about 60% to about 80%, about 70% to about 80%), about 10% to about 70%, about 20% to about 70%, about 30% to about 70%, about 40% to about 70%, about 50% to about 70%, about 10% to about 50%, about 20% to about 50%, about 30% to about 50%, about 40% to about 50% (or any range or value therein) of the water that was present in the composition or solution prior to initiating the drying process. A partially dried composition can be dried further such that it contains less water than when the further drying began.

In some embodiments, a solid composition of the present disclosure can include a hydration level of about 0 to about 10 g water per gram of dried protein (e.g., up to about 10 g water per gram of dried protein; e.g., about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.5, 3, 3.5, 4, 4.5, 6, 6.5, 7, 7.5, 8, 8.5, 9, 9.5, 10, and any range or value therein), though other hydration levels are contemplated. In at least one embodiment, a solid composition can include a hydration level of about 0 g to about 1 g water per gram of dried protein.

The amount of IDP in a composition of the present disclosure can vary depending on the biological material, whether it is a liquid or a solid, and/or whether the composition is a liquid composition that will be dried. Thus, and in some embodiments, the IDP concentration in a liquid composition, a solid composition, and/or other composition described herein can be from about 1 g/L to about 100 g/L or any range or value therein (e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 g/L, or any range or value therein), though higher and lower concentrations are contemplated. In at least one embodiment, the IDP concentration in a liquid composition can be from about 5 g/L to about 70 g/L, such as from about 10 g/L to about 60 g/L, such as from about 30 g/L to about 40 g/L, though high and lower concentrations are contemplated. In some embodiments, the IDP concentration in a solid composition can be from about 1 g/L to about 20 g/L, or from about 1 g/L to about 10 g/L, such as about 5 g/L, though high and lower concentrations are contemplated.

In some embodiments, a composition described herein can include about 50% to about 99.9% of IDP (total weight) (e.g., about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.99% total weight, or any range or value therein), though high and lower amounts are contemplated. For example, and in at least one embodiment, a composition described herein can include about 90% to 99.99% of IDP (total weight) (e.g., about 90, 91, 92, 93, 94, 95, 96, 97, 98, 99, 99.1, 99.15, 99.2, 99.25, 99.3, 99.35, 99.4, 99.45, 99.5, 99.55, 99.6, 99.65, 99.7, 99.75, 99.8, 99.85, 99.9, 99.95, 99.99% total weight, and any range or value therein).

In some embodiments, a mass ratio of the at least one biological material to the at least one IDP in a composition described herein can be from about 1:100 to about 1:1 (e.g., about 1:100, 1:95, 1:90, 1:85, 1:80, 1:75, 1:70, 1:65, 1:60, 1:55, 1:50, 1:45, 1:40, 1:35, 1:30, 1:25, 1:20, 1:15, 1:10, 1:5, 1:1 or any range or value therein), though other mass ratios are contemplated. In at least one embodiment, the mass ratio of the at least one biological material to the at least one IDP in a composition described herein can be from about 100:1 to about 1:1 (e.g., about 100:1, 95:1, 90:1, 8:15, 80:1, 75:1, 70:1, 65:1, 60:1, 55:1, 50:1, 45:1, 40:1, 35:1, 30:1, 25:1, 20:1, 15:1, 10:1, 5:1, 1:1 or any range or value therein), though other mass ratios are contemplated.

In some embodiments, the solid compositions, liquid compositions, and/or other compositions described herein further include one more excipients. Illustrative, but non-limiting, excipients include trehalose, sucrose, maltose, bovine serum albumin, human serum albumin, mannitol, sorbitol, polysorbate, a salt, water, a buffer, an antioxidant, a preservative, a colorant, a flavorant, or combinations thereof.

In some embodiments, when a composition described herein includes an excipient, the concentration of an individual excipient (or the concentration of all excipients) in the composition can be from about 0.01 wt % to about 99 wt % of the total composition or any range or value therein (e.g., about 0.01 wt %, 0.02 wt %, 0.03 wt %, 0.04 wt %, 0.05 wt %, 0.06 wt %, 0.07 wt %, 0.08 wt %, 0.09 wt %, 0.1 wt %, 0.2 wt %, 0.3 wt %, 0.4 wt %, 0.5 wt %, 0.6 wt %, 0.7 wt %, 0.8 wt %, 0.9 wt %, 1 wt %, 1.5 wt %, 2 wt %, 2.5 wt %, 3 wt %, 3.5 wt %, 4 wt %, 4.5 wt %, 5 wt %, 6 wt %, 7 wt %, 8 wt %, 9 wt %, 10 wt %, 15 wt %, 20 wt %, 25 wt %, 30 wt %, 35 wt %, 40 wt %, 45 wt %, 50 wt %, 55 wt %, 60 wt %, 65 wt %, 70 wt %, 75 wt %, 80 wt %, 85 wt %, 90 wt %, 95 wt % or 99 wt %, or any range or value therein), though other amounts are contemplated. In at least one embodiment, the concentration of an individual excipient (or the concentration of all excipients) in the composition is from about 0.01 wt % to about 10 wt %, such as those amounts or ranges described above.

In some embodiments, the concentration of an individual excipient (or the concentration of all excipients) in the mixture can be from about 0.01 mM to about 100 mM or any range or value therein (e.g., about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, 15, 20, 25, 30, 35, 40, 45, 50, 55, 60, 65, 70, 75, 80, 85, 90, 95, 100 mM, any range or value therein), though other amounts are contemplated.

As a non-limiting example, and in some embodiments, a salt concentration of the composition can be about 0.1 mM to about 50 mM and any value or range therein). Any appropriate physiologically compatible salt can be used, for example, NaCl.

The pH of a composition described herein can be from about 5 to about 9, or any range or value therein (e.g., about 5, 5.1, 5.2, 5.3, 5.5, 5.6, 5.7, 5.8, 5.9, 6, 6.1, 6.2, 6.3, 6.5, 6.6, 6.7, 6.8, 6.9, 7, 7.1, 7.2, 7.3, 7.5, 7.6, 7.7, 7.8, 7.9, 8, 8.1, 8.2, 8.3, 8.5, 8.6, 8.7, 8.8, 8.9, 9, and the like), though higher or lower pH values are contemplated. In at least one embodiment, the pH of a composition described herein is, e.g., from about 6 to about 8, such as from about 6.5 to about 7.5, such as from about 6.5 to 7 or from about 7 to 7.5.

Embodiments of the present disclosure also relate to methods of forming the compositions described above, methods of stabilizing at least one biological material, and to methods of forming a stabilized biological material. As discussed above, reference to "biological material" includes reference to "biological material," biological material of interest," biologically-derived material," and "biologically-derived material of interest" unless the context indicates otherwise.

In at least one embodiment, both of these methods generally include introducing or contacting the first component comprising at least one IDP (e.g., at least one TDP and/or at least one modified TDP) with the second component comprising at least one biological material to form the composition comprising the at least one IDP and the at least one biological material, thereby, e.g., stabilizing the at least one biological material. Introducing can be performed under conditions that include suitable temperatures, pressures, and rates of introduction of the IDP with the biological material. The conditions can also include mixing the components of the composition by any suitable mixing process.

In some embodiments, the method further includes removing at least a portion of the liquid content of the composition. The liquid content can include aqueous material. Removing at least a portion of the liquid content can include drying, or at least partially drying, the composition that includes the at least one IDP and the at least one biological material. Any suitable method of drying can be utilized such as, e.g., evaporating, dehydrating, desiccating, vacuum desiccating, vacuum drying, air drying, spray drying, freeze drying, spray-freeze drying, lyophilizing, foam drying, or combinations thereof, among other suitable methods As described above, the composition can be in the form of, e.g., a solid (such as particles and/or powders) and/or a liquid. The at least partially drying can be performed during methods of forming the solid composition and/or liquid composition.

When a liquid composition is desired, and in some embodiments, the methods described herein include introducing or contacting the first component comprising at least one IDP (e.g., at least one TDP and/or at least one modified TDP) with the second component comprising at least one biological material to form the liquid composition comprising the at least one IDP and the at least one biological material, thereby, e.g., stabilizing the at least one biological material. In at least one embodiment, a third component that includes an aqueous material (e.g., water, buffer, et cetera), an organic material (e.g., an alcohol such as ethanol), an excipient, an additive, or combinations thereof can be introduced to the first component and/or second component prior to introducing, during introducing the first and second components, and/or after introducing the first and second components. In some examples, the first component and/or second component can already be present in the form of a solution/suspension with a third component. In such cases, for example, addition of a third component can be optional. Drying, or at least partially drying, can be performed if desired.

When a solid or substantially solid composition is desired, and in some embodiments, the methods described herein generally include forming a liquid composition and then forming a solid composition from the liquid composition. In some embodiments, this method includes introducing (or contacting) the first component comprising at least one IDP (e.g., at least one TDP and/or at least one modified TDP) with the second component comprising at least one biological material to form the liquid composition comprising the at least one IDP and the at least one biological material. Introducing can be performed as described above. The method optionally includes use of a third component as described above. The solid composition (or substantially solid composition) can then be formed by drying, or at least partially drying, the liquid composition according to suitable methods described above.

Embodiments of the present disclosure, as described herein, include methods of forming the compositions comprising at least one IDP (which may be modified); and at least one biological material of interest and/or at least one biologically-derived material of interest. Embodiments also include methods of stabilizing at least one biological material of interest and/or at least biologically-derived material of interest. Embodiments described herein also include methods of forming a stabilized biological material of interest and/or stabilized biologically-derived material of interest.

In certain embodiments, methods described herein include introducing or contacting at least one biological material of interest and/or biologically-derived material of interest with at least one IDP (e.g., a modified TDP), to produce a liquid composition that includes the at least one biological material of interest and the at least one IDP, thereby stabilizing the at least one biological material of interest. In certain embodiments, methods described herein include introducing or contacting at least one biological material of interest and/or biologically-derived material of interest with at least one IDP (e.g., a modified TDP), to produce a liquid composition comprising the at least one biological material of interest and/or biologically-derived material of interest and the at least one IDP; and at least partially drying the liquid composition to produce a solid composition comprising the at least one biological material of interest and/or biologically-derived material of interest and the at least one IDP, thereby stabilizing the at least one polypeptide and/or peptide of interest.

Embodiments described herein also generally relate to uses of the compositions described herein. As described above, the IDPs impart drought or desiccation resistance/tolerance to a biological material. Once the composition comprising the at least one IDP and the at least one biological material is ready for its intended purpose, the composition can be mixed with another component, e.g., a carrier, buffer, et cetera.

As a non-limiting example, a pharmaceutical formulation (or a portion thereof) can be prepared by contacting the at least one biological material with the at least one IDP, which is then dried to form a powder composition (e.g., a composition described above). When the pharmaceutical formulation is ready to be, e.g., administered to a patient or animal, the composition in the form of a powder can be reconstituted in, e.g., a buffer, and then administered to the patient or animal. Any other biological material described herein can be formulated with the IDP and reconstituted in the same or similar manner.

Kits are also contemplated. In some embodiments, a kit can include at least one IDP described herein in, e.g., a form for stabilizing a biological material (e.g., a vaccine, antibody, et cetera). In some embodiments, the kit includes one or more additional components, such as carriers, buffers, therapeutic agents, diagnostic agents, food agents, or other components suitable for the intended use. A kit for use in stabilizing a biological material can include at least one IDP described herein such as, but not limited to, an amino acid sequence having at least about 50%, at least about 60%, at least about 70%, at least about 80%, at least about 90%, or at least about 95% identity to any one of SEQ ID NOs: 4, 6, 8, 10, 12, 14, 16, 18, 20, 22, 24, 26, 28, 30, 32, or a complement thereof; and/or an amino acid sequence encoded by a nucleotide sequence having at least about 50%, at least about 60%, at least about 70%, at least about 80%, at least about 90%, or at least about 95% identity to any of SEQ ID NOs: 3, 5, 7, 9, 11, 13, 15, 17, 19, 21, 23, 25, 27, 29, 31, or a complement thereof.

Embodiments of the present disclosure can be further understood by the following non-limiting examples. The following examples are put forth so as to provide those of ordinary skill in the art with a complete disclosure and description of how to make and use aspects of the present disclosure, and are not intended to limit the scope of aspects of the present disclosure.

Examples

Cloning. All variants and wild type CAHS D were cloned into the pET28b expression vector using Gibson assembly methods. Primers were designed using the NEBuilder tool (New England Biolabs, Ipswitch, MA) and inserts were synthesized as gBlocks and purchased from Integrated DNA Technologies (Integrated DNA Technologies, Coralville, IA).

Protein Expression. Expression constructs were transformed in BL21 (DE3) *E. coli* (New England Biolabs) and plated on lysogeny broth (LB) agar plates containing about 50 µg/mL Kanamycin. At least 3 single colonies were chosen for each construct and tested for expression. Large-scale expression was performed in about 1 L LB/Kanamycin cultures, shaken at about 37° C. (Innova S44i, Eppendorf, Hamburg, Germany) until an $OD_{600}$ of about 0.6, at which point expression was induced using about 1 mM isopropyl-β-D-thiogalactopyranoside (IPTG). Protein expression continued for about four hours, after which cells were collected at ~4000 g at about 4° C. for about 30 minutes. Cell pellets were resuspended in about 10 mL of resuspension buffer (~20 mM tris, pH ~7.5, ~30 µL protease inhibitor (Sigma Aldrich, St. Louis, MO). Pellets were stored at about ~80° C.

Protein Purification. Bacterial pellets were thawed and heat lysis was performed. Pellets were boiled for five minutes and allowed to cool for about 10 minutes. All insoluble components were removed via centrifugation at about 5,000 g at about 10° C. for about 30 minutes. The supernatant was sterile filtered with 0.45 µm and 0.22 µm syringe filters (Foxx Life Sciences, Salem, NH). The filtered lysate was diluted (~1:2) in purification buffer UA (about 8 M Urea, about 50 mM sodium acetate [Acros Organics, Carlsbad, CA], pH ~4). The protein was then purified using a cation exchange HiPrep™ SP HP 16/10 (Cytiva, Marlborough, MA) on an AKTA Pure 25 L (Cytiva), controlled using a UNICORN 7 Workstation pure-BP-exp (Cytiva). Variants were eluted using a gradient of about 0-50% UB (about 8 M Urea, about 50 mM sodium acetate, and about 1 M NaCl, pH ~4), over 20 column volumes.

Fractions were assessed by SDS-PAGE (sodium dodecyl sulphate-polyacrylamide gel electrophoresis) and pooled for dialysis in 3.5 KDa. MWCO dialysis tubing (SpectraPor™3 Dialysis Membrane, Sigma Aldrich). MWCO refers to the molecular weight cutoff and refers to the smallest mass of a protein that will be retained in the tubing. For all variants except CLC, pooled fractions were dialyzed at about 25° C. for about four hours against a urea solution (~2 M urea, ~20 mM sodium phosphate at pH ~7), then transferred to a sodium phosphate solution (~20 mM sodium phosphate at pH ~7) overnight. This was followed by six rounds of about 4 hours each in Milli-Q® water (~18.2 MΩcm). Dialyzed samples were quantified fluorometrically (Qubit™ 4 Fluorometer, Invitrogen, Waltham, MA), aliquotted in the quantity needed for each assay, lyophilized (FreeZone® 6, Labconco, Kansas City, MO) for about 48 hours, then stored at about ~20° C. until use. CLC was dialyzed in a urea solution (~2 M urea, ~20 mM Tris at pH ~7) for about four hours, followed by 6 rounds of about 4 hours each in a Tris solution (~20 mM Tris at pH ~7). CLC samples were quantified using the Qubit™ 4 Fluorometer as described, concentrated using Amicon spin-concentrators (Sigma-Aldrich) to the desired concentration, and used immediately.

As described above, CAHS proteins, such as CAHS D proteins, enable tardigrades to survive desiccation and are effective protectants of biological material in the dry state, outcompeting well known excipients. At high concentrations, CAHS D proteins have an increased propensity to form gels at high concentration. The examples include investigations into modified CAHS D proteins.

FIGS. 1A-1D show exemplary cone-plate rheological analysis data for the gelation of CAHS proteins at various concentrations. FIGS. 1A-1D also show the concentration dependence and strength of gelation versus time. Generally, with the increased concentration of CAHS protein from about 7.5 g/L (FIG. 1A) to about 60 g/L (FIG. 1B), the storage modulus passed the loss modulus faster—indicating gelation has occurred—with a higher strength value. The solution of about 7.5 g/L CAHS protein remained relatively diffuse over much of the time tested (FIG. 1A). The data in FIG. 1B showed that the solution of about 30 g/L CAHS protein becomes much more viscous at an earlier time point, while the data of FIGS. 1C and 1D indicated that the solutions of about 45 g/L and about 60 g/L, respectively, form robust gels.

Figure 2B:
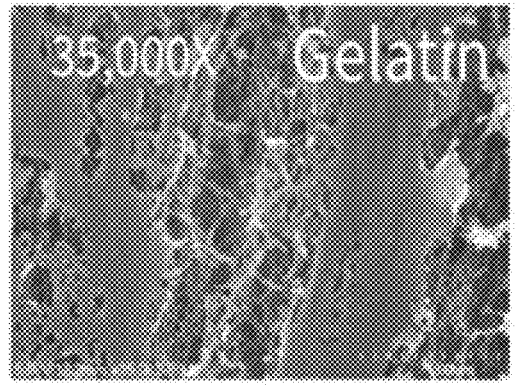
FIG. 2B is a SEM image of gelatin at 35,000× magnification according to at least one embodiment of the present disclosure.
Figure 2C:
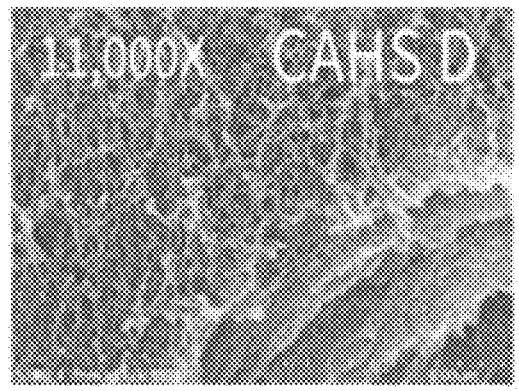
FIG. 2C is an exemplary SEM image of CAHS D protein at 11,000× magnification according to at least one embodiment of the present disclosure.
Figure 2D:
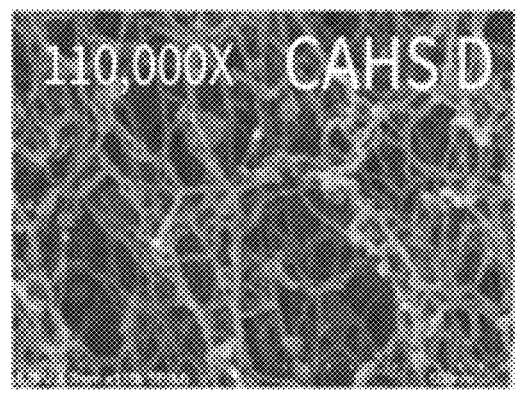
FIG. 2D is an exemplary SEM image of CAHS D protein at 110,000× magnification according to at least one embodiment of the present disclosure.

FIGS. 2A-2D show exemplary scanning electron microscope (SEM) images comparing the morphology of CAHS D to other proteins. Specifically, FIG. 2A is a SEM image of lysozyme at 248× magnification, and FIG. 2B is a SEM image of gelatin at 35,000× magnification. FIGS. 2C and 2D are SEM images of CAHS D at 11,000× magnification and 110,000× magnification, respectively. All SEM imaging was performed with the proteins at about 50 g/L using a Hitachi S-47000 scanning electron microscope. Lysozyme is a non-gelling protein, while gelatin is a gelling protein. The SEM images confirmed the gelling nature of CAHS proteins, showing that the web-like reticular nature of the CAHS 1) gel structure is similar to that of gelatin.

Overall, the high-resolution imaging revealed that CAHS D gels form reticular networks with a fine meshwork of CAHS D fibers interspersed with large pores. This topology is similar to gels formed by gelatin, and morphologically distinct from crystalline solids formed by lysozyme.

The inventor has determined that client molecules (e.g., biological material and/or biologically-derived material) embedded and/or dispersed within a CAHS gel may not be all protected equally. Such unequal protection may be due to the amorphous characteristics of the gel. To investigate this phenomenon and to probe matrix effects on conformational protein dynamics, the photosynthetic reaction center (RC) from the bacterium Rhodobacter sphaeroides was embedded in a CAHS protein matrix and the integrity thereof analyzed. This membrane-spanning pigment-protein complex catalyzes the primary photochemical events of bacterial photosynthesis. Following absorption of a photon, the primary electron donor (P) of the reaction center, which is a bacteriochlorophyll dimer situated near the periplasmic side of the protein, delivers an electron to the primary quinone acceptor, $Q_A$, located ~25 Å away from P and closer to the cytoplasmic side of the RC. This electron transfer process, occurring in about 200 ps, generates the primary charge separated state, $P^+Q^-$. In the absence of the secondary quinone acceptor bound at the $Q_B$ site (or in the presence of inhibitors which block electron transfer from $Q_A^-$ to $Q_B$), the electron on $Q_A^-$ recombines with the hole on $P^+$ by direct electron tunneling. The kinetics of $P^+Q_A^-$ recombination after a short (nanosecond) flash of light provides an endogenous probe of the RC conformational dynamics.

Figure 3:
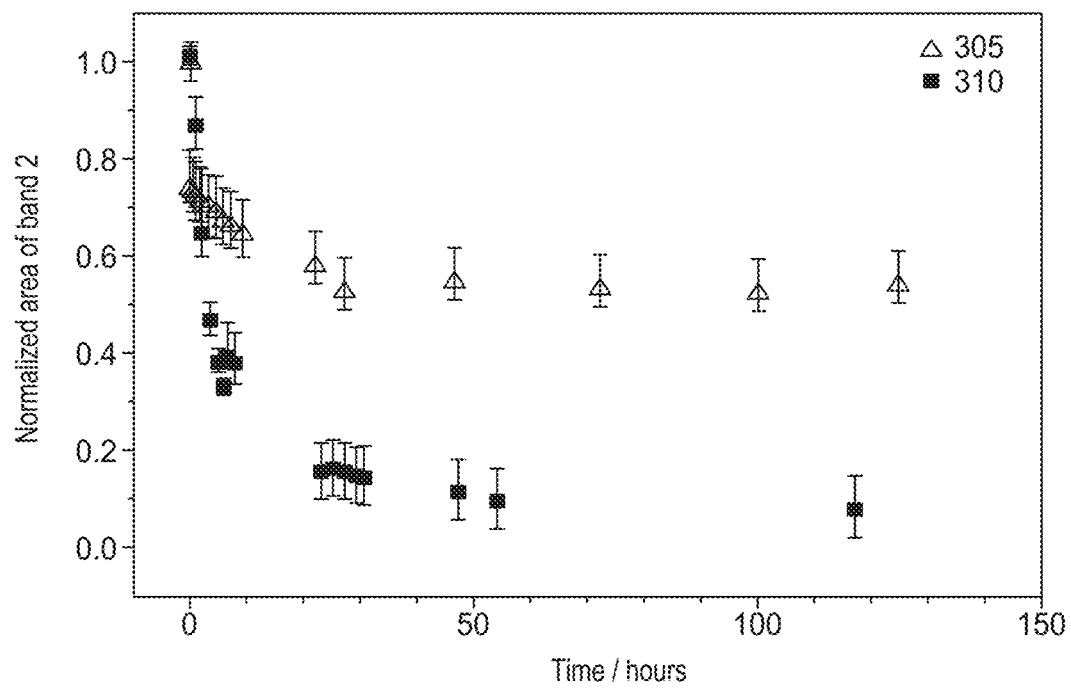
FIG. 3 illustrates a comparative stability analysis of non-embedded polypeptides versus polypeptides embedded in a CAHS protein matrix according to at least one embodiment of the present disclosure.

FIG. 3 illustrates a comparison of the stability of the RC embedded in the CAHS protein matrix (Ex. 305) as compared to non-embedded RC in film (Ex. 310). When dried, the RC in film (Ex. 310) rapidly underwent breakdown until essentially all of the RC had denatured. Interestingly, RC embedded in the CAHS protein matrix (Ex. 305) also underwent an initial rapid breakdown, but the breakdown stabilized with ~60% of the embedded RC remaining stable for the duration of the experimental period. These results indicated a biphasic breakdown of RC within the CAHS protein matrix and the formation of two RC populations: one that was not fully stabilized and one that was highly stable.

For the data shown in FIG. 3, the following sample preparation was performed. About 78 µL of RCs purified from Rhodobacter sphaeroides R26 at ~76 µM concentration in assay buffer (~10 mM Tris, ~0.025% lauryldimethylamine oxide (LDAO), pH ~8.0) was mixed with about 64 µL of about 16 g/L CAHS protein in water, and about 8 µL of an o-phenanthroline solution (~200 mM o-phenanthroline in ethanol). O-phenanthroline is an inhibitor that blocks $Q_A^-$ to $Q_B$ electron transfer, thereby allowing the recombination kinetics of the $P^+Q_A^-$ state to be monitored. The lyophilized CAHS protein was dissolved in water and heated to about 50° C. for about 5 minutes. The protein was allowed to cool to room temperature, and during this cooling it was rapidly mixed with the RC suspension prior to gel formation. This mixture was immediately layered on a 50 mm diameter $CaF_2$ optical window and dried under N2 flow for about 5 minutes. The sample was then inserted into the gas-tight holder and equilibrated at a RH=11% in the presence of LiCl. The glassy matrix was characterized by a (CAHS/RC) molar ratio of about 6.6, corresponding to a mass ratio of about 1.7. This ratio was chosen for comparison with previous results of strongly inhibited RC conformational dynamics when embedded in glassy trehalose matrices.

As shown with the data presented in FIG. 3, the formation of two RC subpopulations was likely the result of gelation of CAHS proteins causing an amorphous matrix. The inventor further investigated the driving factors behind CAHS gelation in order to develop methods for preventing gel formation, which reduce heterogeneity and improve CAHS protection capability. To prevent (or at least mitigate) gelation, the inventor analyzed the conformational ensemble that CAHS proteins are predicted to adopt, as well as the binding propensity of different regions within the CAHS protein.

Figure 4:
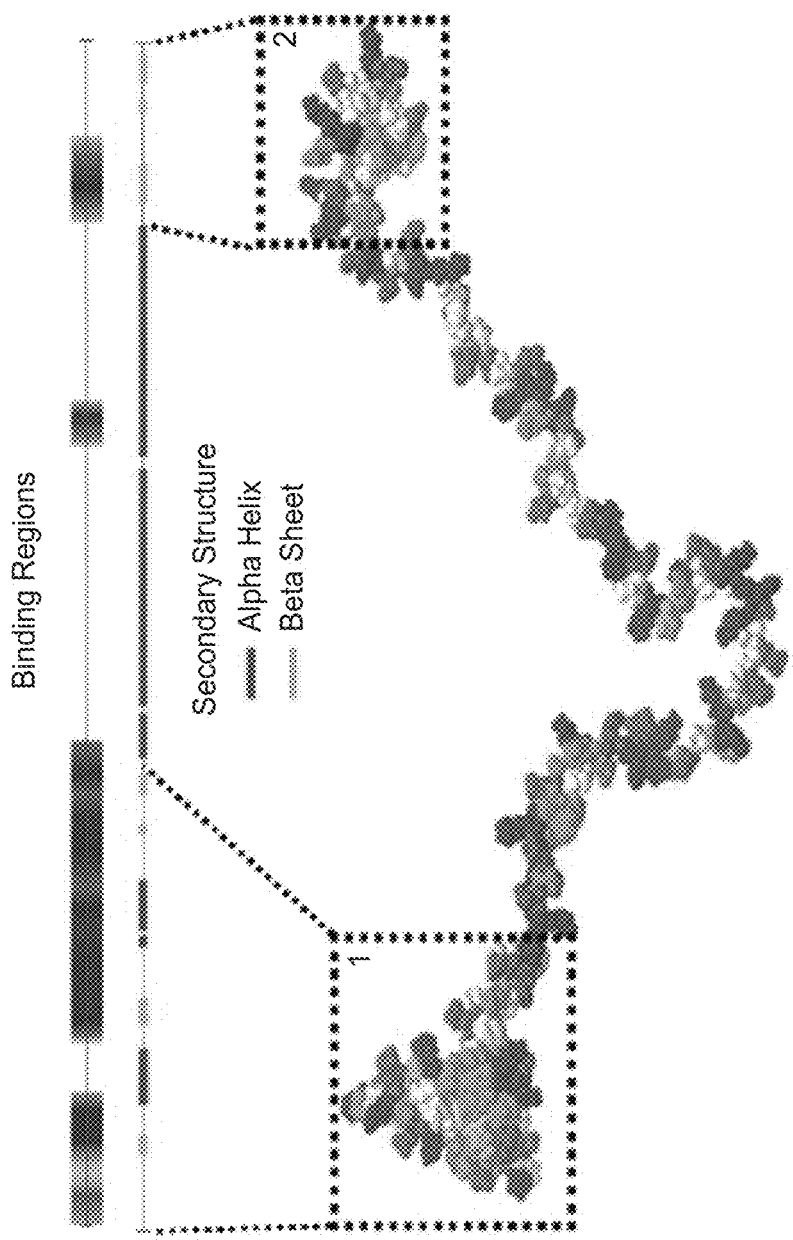
FIG. 4 is an illustration of a predicted ensemble model of a CAHS D protein structure according to at least one embodiment of the present disclosure.

An all-atom Monte Carlo simulation was performed to assess the predicted ensemble-state adopted by monomeric CAHS D proteins. FIG. 4 is an illustration of a predicted ensemble model of a CAHS D protein structure according to at least one embodiment of the present disclosure. Specifically, FIG. 4 shows an exemplary bioinformatic prediction of secondary structure characteristics (top) and representative conformational global ensemble model (bottom) of an example CAHS D protein. The predicted binding regions/binding capacity, indicated in blue, as well as the secondary structure, including helices in red and beta-sheets in green, are mapped in the predicted ensemble model. The simulations revealed a dumbbell-like ensemble, with the N- and C-termini of the CAHS D protein forming relatively collapsed regions (indicated by reference numerals 1 and 2) that are held apart from one another by an extended and highly charged linker region. The binding regions/binding capacity matches with the beta sheets. Meta-stable transient helices were observed throughout the linker region and transient beta sheets were observed in the collapsed N- and C-terminal regions 1, 2, resulting in the collapsed regions being "sticky" with high binding/interaction capacity. Overall, the simulations indicated that CAHS D exists in a dumbbell-like ensemble, which moves through conformational states. The simulations also indicated that the termini are highly beta-sheeted, with such termini being held apart by an extended and largely alpha-helical linker.

The molecular architecture of CAHS D proteins also indicated that gelation can be driven by interactions between the two "sticky" terminal regions 1, 2. For example, the terminal regions 1, 2 of a single CAHS D protein will likely not interact with each other due to such regions being held apart by the intervening extended linker region. However, at high concentrations of CAHS D protein, the terminal regions 1, 2 of adjacent or nearby CAHS D proteins can interact with each other, leading to polymerization and, ultimately, gelation.

To further analyze the mechanism for gelation, a series of mutant CARS D protein constructs with mutations that disrupt the characteristic dumbbell-like architecture of the CAHS D protein were generated and observed along with the wild type CAHS D protein.

FIG. 5 illustrates a schematic representation of the aforementioned mutant CAHS D protein constructs and wild type CAHS D protein ("WT CAHS D"; SEQ ID NOs: 1, 2) and whether gelation was present or absent at high concentrations thereof, according to embodiments of the present disclosure. The mutant CAHS D protein constructs include an "NL1" construct missing the C-terminus and at least a portion of the linker region (SEQ ID NOs: 9, 10), "CL1" construct missing the N-terminus and at least a portion of the linker region (SEQ ID NOs: 11, 12), "N" construct having only the N-terminus (SEQ ID NOs: 3, 4), "L" construct having only the linker region (SEQ ID NOs: 5, 6), "C" construct having only the C-terminus (SEQ ID NOs: 7, 8), and "0.5× Linker" construct having a shortened linker region (0.5× the wild type; SEQ ID NOs: 13, 14). For reference, the shaded sphere indicates an N-terminus of the CAHS D protein structure, the open sphere indicates the C-terminus of the CAHS D protein structure, and the linker is the wavy line connecting the two termini. As shown in FIG. 5, disruptions to the dumbbell-like structure of the CAHS D proteins can prevent gelation from occurring.

Figure 6:
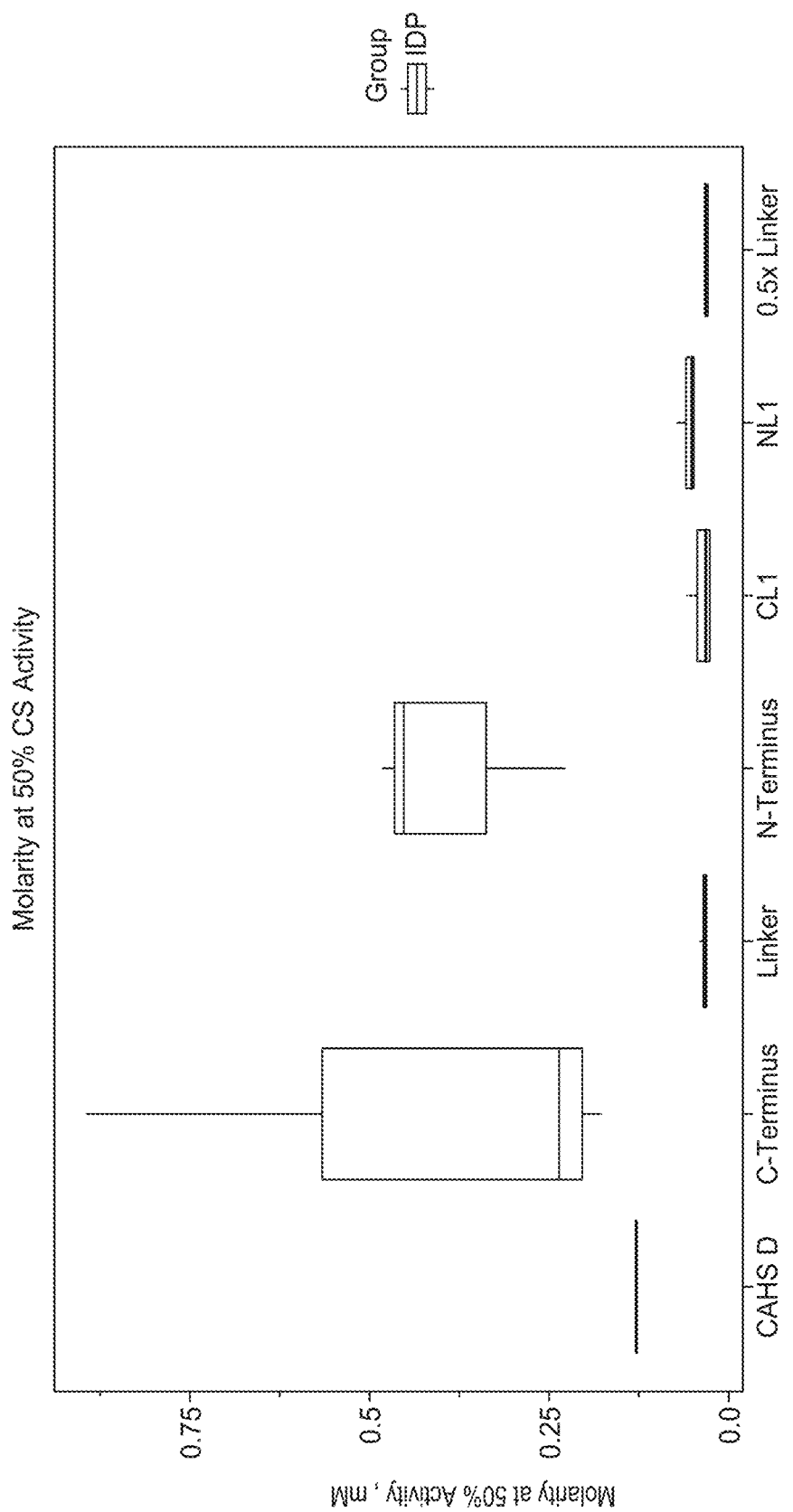
FIG. 6 shows exemplary data for the analysis of molarity of example mutant CAHS protein constructs at which 50% activity of citrate synthase is preserved according to at least one embodiment of the present disclosure.

To determine the effect of gelation-related heterogeneity within dried CAHS D matrices, both gelling and non-gelling mutant CAHS D protein constructs were observed for their ability to prevent drying-induced aggregation and inactivation of a citrate synthase enzyme. FIG. 6 illustrates an analysis of molarity of mutant CAHS D protein constructs at which ~50% activity of the citrate synthase (CS) enzyme is preserved according to embodiments of the present disclosure. Here, the protective capacity of the wild-type CAHS 1) protein (indicated as "CAHS D" in FIG. 6) and the various mutant protein constructs were investigated. The mutant protein constructs are indicated as C-terminus, linker, N-terminus, CL1, NL1, and 0.5× linker. The y-axis shows the molarity at which 50% activity (mM) is preserved; that is, the y-axis shows the amount of protectant (wild type or mutant) is needed to preserve 50% enzyme activity. A lower value of the molarity at 50% activity indicates a lower amount of wild-type CAHS D protein or mutant CAHS D protein constructs needed.

As shown in FIG. 6, several of the non-gelling mutant constructs can provide increased protective capacity relative to the wild-type CAHS protein, while other non-gelling mutant constructs did not under the conditions tested. A common feature of the non-gelling mutants that provided increased protection was the presence of all or some of the extended linker, with the linker alone (shown as linker and 0.5× linker mutants) providing the highest levels of protection. Mutant constructs that could not gel but also lacked the linker regions (C-terminus and N-terminus mutants in FIG. 6) provided less protection than the wild-type CAHS protein. Thus, under the conditions tested, it is believed that a main driver of CAHS D-mediated protection against desiccation can be the linker region, and that the terminal regions, which allow for gelation, can be dispensable. Furthermore, in some examples, the presence of the terminal regions can inhibit protection since the terminal regions may drive gelation.

The following citrate synthase assay protocol was utilized for the data shown in FIG. 6.

Citrate Synthase Assay Protocol

The assay protocol described below was designed to be conducted in triplicate for 10 concentrations of a molecule or protein of interest. Materials and reagents utilized for this assay protocol included commercially available materials and reagents from Sigma-Aldrich, including a citrate synthase kit (Sigma-Aldrich Cat. CS0720), Assay Buffer for Citrate Synthase 5× (Assay Buffer, Sigma-Aldrich Cat. B6935), 5,5'-Dithiobis-2-nitrobenzoic acid (DTNB, Sigma-Aldrich Cat. D8130), acetyl coenzyme A trilithium salt (Acetyl CoA, Sigma-Aldrich Cat. A2181), oxaloacetic acid (OAA, Sigma-Aldrich Cat. O4126), and citrate synthase (Sigma-Aldrich Cat. C3260).

To prepare the buffer, the Assay Buffer 5× was first thawed and stored at about 4° C., and then diluted to make about 25 mL of Assay Buffer 1× prior to experimentation. Acetyl CoA was dissolved in about 1 mL of purified $H_2O$ and distributed into ~160 μL aliquots. DTNB was dissolved in about 1 mL of ethanol and distributed into ~160 μL aliquots.

To prepare a protein of interest, lyophilized protein was re-suspended in at least 200 μL of $H_2O$. Increments of ~50 μL of $H_2O$ were optionally added until the protein was completely soluble. Protein concentration was then quantified via a Modified Lowry Assay commercially available from Bio Basic (Bio Basic Cat. SK4041) following the manufacturer's protocol.

Upon preparation of the buffer and protein of interest, ~9 μL dilutions of the protein of interest were made in purified $H_2O$ in the desired concentration range and aliquotted into microcentrifuge tubes in triplicate, along with controls having 0 mM concentration. For the control samples, ~9 μL dilutions of the protein of interest were made in Assay Buffer 1× and aliquotted into microcentrifuge tubes in triplicate, ensuring that controls at 0 mM concentration were included.

About 1 μL of citrate synthase was then added to the experimental samples, but not the control samples. The microcentrifuge tubes with experimental samples were immediately stored on ice thereafter, while the control samples were stored at about 4° C. The experimental samples were desiccated in a Speedvac™ for five increments of about 1 hour each. The experimental samples were re-suspended in ~10 μL of purified $H_2O$ after each 1-hour increment. Between resuspensions, the microcentrige tubes with the experimental samples were kept on ice. After the last round of desiccation, each experimental sample was re-suspended in ~10 μL of Assay Buffer 1× and kept on ice.

1 aliquot each of Acetyl CoA and DTNB were then thawed, and ~140 μL of each were thereafter added to ~12.88 mL of Assay Buffer 1×, thus forming the reaction mixture. The reaction mixture was kept on ice. OAA (about 3.9 mg) was added to 3 mL of Assay Buffer 1× and kept on ice.

About 1 μL of citrate synthase was then added to each control sample, and the microcentrifuge tubes with the control samples were kept on ice. About 2 μL of each sample solution were added to a microplate well and gently mixed with about 188 μL of the reaction mixture by pipette. The microplate was maintained on ice during loading of the wells with samples. The plate reader was set to measure sample absorbance at 412 nm every 10 seconds for about 1.5 minutes at ~25° C., and was equilibrated at ~25° C. for about five minutes prior to running the samples. Thereafter, OAA (about 10 μL) was added to each sample well and the kinetic absorbance of the samples was measured via the plate reader.

Another investigation of whether gel formation of CAHS D occurs through inter-protein beta-sheet interactions mediated between termini was performed using a wild-type CAHS D protein and a range of CAHS D variants. FIG. 7 illustrates a schematic representation of mutant CAHS D protein constructs and whether gelation was present or absent at high concentrations thereof, according to embodiments of the present disclosure. Wild-type CAHS protein ("WT CAHS D"; SEQ ID NOs: 15, 16) are shown and the mutant constructs include the following: a "linker region (LR)" construct (SEQ ID NOs: 17, 18); a "NLN" construct having two N-termini connected by a linker (SEQ ID NOs: 19, 20); a "CLC" construct having two C-termini connected by a linker (SEQ ID NOs: 21, 22); a "CL2" construct missing the N-terminus and at least a portion of the linker region (SEQ ID NOs: 23, 24); a "NL2" construct missing the C-terminus and at least a portion of the linker region (SEQ ID NOs: 25, 26); a "2× linker (2×LR)" construct having a longer linker region that is 2× the wild type (SEQ ID NOs: 27, 28); a "N-terminus" construct having only the N-terminus (SEQ ID NOs: 29, 30), and a "FL-proline" construct having the same sequence as the wildtype CAHS D protein with prolines inserted every 6-8 amino acids (SEQ ID NOs: 31, 32). For reference, the shaded sphere indicates an N-terminus of the CAHS protein structure, the open sphere indicates the C-terminus of the CAHS protein structure, and the linker is the wavy line connecting the two termini. As shown, disruptions to the dumbbell-like structure of the CAHS proteins can prevent gelation from occurring.

All variants lacking at least one termini resulted in a loss of gelation (N, LR, FL-Proline, NL2, CL2). Unexpectedly, variants that replaced one terminal region for another (NLN and CLC) also did not form gels under the conditions tested. These results indicated that heterotypic interactions between N- and C-termini are related to strong gel formation, implicating molecular recognition and specificity encoded by the termini. The 2× linker (2×LR) variant, which maintained heterotypic termini but doubled the length of the linker, gelled rapidly at about 5 g/L (~0.1 mM) under the conditions tested, well below the gelling point of the wild-type protein at about 15 g/L (~0.6 mM). This result indicated that the length of the linker can tune the gel point by determining the monomeric molecular volume and/or setting the overlap concentration, which can be a key determinant of the gel point.

For the results shown in FIG. 7, the following citrate synthase protection assay was performed. The Citrate Synthase Kit (Sigma-Aldrich) was adapted for use in this assay. All samples were prepared in triplicate, except desiccated negative control samples, which were prepared in quadruplicate, so that the extra sample could be used for assessment of desiccation efficiency. The concentration of gelatin (Sigma-Aldrich) was determined based on an average mass of ~150 kDa. Lyophilized variants were resuspended in either purified water (samples to be desiccated) or 1× Assay Buffer (control samples) to a concentration of about 20 g/L and diluted as necessary for lower concentrations. Citrate synthase (Sigma-Aldrich) was added at a ratio of ~1:10 to resuspended protectants. Non-desiccated control samples were measured immediately following resuspension as described in the protocol described above for FIG. 6. Desiccated samples were subjected to 5-6 rounds of desiccation and rehydration (1-hour Speedvac™ desiccation [Thermo Fisher Scientific] followed by resuspension in water). Following the fifth round of desiccation, a negative control sample was resuspended and assayed to determine if activity remained. If the negative control sample retained more than 10% activity, a sixth round of desiccation/rehydration was performed. After the final round of desiccation, samples were resuspended in ~10 µL of cold 1× Assay Buffer. Samples were diluted ~1:100 in the assay reaction mixture supplied, and all subsequent steps followed the protocol described above for FIG. 6. The colorimetric reaction was measured for 90 seconds at 412 nm using the Spark 10M (Tecan).

Embodiments of the present disclosure generally relate to methods and compositions for stabilizing biological material using intrinsically disordered proteins. Embodiments compositions described herein include intrinsically disordered proteins modified to prevent polymerization thereof and the formation of gel-like matrices, thus improving the ability of the intrinsically disordered proteins to protect and stabilize sensitive biological materials.

Embodiments of the present disclosure, as described herein, include liquid compositions, solid compositions, or other compositions for stabilizing biological material, and to methods of forming such compositions. The compositions include at least one IDP (such as a modified tardigrade disordered protein). The compositions further include at least one biological material of interest, at least one biologically-derived material of interest, or both. Embodiments described herein also include an isolated polypeptide comprising an amino acid sequence of any one of SEQ ID NOs: 4, 6, 8, 10, 12, 14, 16, 18, 20, 22, 24, 26, 28, 30, 32, or a complement thereof. Embodiments also include a recombinant nucleic acid construct comprising a nucleotide sequence of any one of the following SEQ ID NOs: 3, 5, 7, 9, 11, 13, 15, 17, 19, 21, 23, 25, 27, 29, 31, or a complement thereof.

As used herein, a "native" or "wild type" nucleic acid, nucleotide sequence, polypeptide, or amino acid sequence refers to a naturally occurring or endogenous nucleic acid, nucleotide sequence, polypeptide, or amino acid sequence. For example, a "wild type mRNA" is an mRNA that is naturally occurring in or endogenous to the organism. A "homologous" nucleic acid sequence is a nucleotide sequence naturally associated with a host cell into which it is introduced. As used herein, "nucleic acid," "nucleotide sequence," and "polynucleotide" are used interchangeably and encompass both RNA and DNA, including cDNA, genomic DNA, mRNA, synthetic (e.g., chemically synthesized) DNA or RNA, chimeras of RNA and DNA, and the like. The term polynucleotide, nucleotide sequence, or nucleic acid refers to a chain of nucleotides without regard to length of the chain. The nucleic acid can be double-stranded or single-stranded. Where single-stranded, the nucleic acid can be a sense strand or an antisense strand. The nucleic acid can be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases.

As used herein, the term "gene" refers to, e.g., a nucleic acid molecule capable of being used to produce mRNA, antisense RNA, miRNA, anti-microRNA antisense oligodeoxyribonucleotide (AMO) and the like. Genes may or may not be capable of being used to produce a functional protein or gene product. Genes can include both coding and non-coding regions (e.g., introns, regulatory elements, promoters, enhancers, termination sequences and/or 5' and 3' untranslated regions). A gene may be "isolated" which means a nucleic acid that is substantially or essentially free from components normally found in association with the nucleic acid in its natural state. Such components include other cellular material, culture medium from recombinant production, and/or various chemicals used in chemically synthesizing the nucleic acid.

The term "isolated" can refer to a nucleic acid, nucleotide sequence, peptide, or polypeptide, or other biological material that is substantially free of cellular material, viral material, and/or culture medium (when produced by recombinant DNA techniques), or chemical precursors or other chemicals (when chemically synthesized). Moreover, an "isolated fragment" is a fragment of a nucleic acid, nucleotide sequence, peptide, or polypeptide, or other biological material that is not naturally occurring as a fragment and would not be found in the natural state. "Isolated" does not mean that the preparation is technically pure (homogeneous), but it is sufficiently pure to provide the nucleic acid, nucleotide sequence, peptide, or polypeptide, or other biological material acid in a form in which it can be used for the intended purpose.

The terms "nucleotide sequence" and "polynucleotide" are used interchangeably. The terms "amino acid sequence," "polypeptide", and "polypeptide sequence" are used interchangeably.

In some embodiments, the recombinant nucleic acid molecules, nucleotide sequences and polypeptides of the present disclosure are "isolated." An "isolated" nucleic acid molecule, an "isolated" nucleotide sequence, or an "isolated" polypeptide is a nucleic acid molecule, nucleotide sequence or polypeptide that, by the hand of man, exists apart from its native environment and is therefore not a product of nature. An isolated nucleic acid molecule, nucleotide sequence or polypeptide may exist in a purified form that is at least partially separated from at least some of the other components of the naturally occurring organism or virus, for example, the cell or viral structural components or other polypeptides or nucleic acids commonly found associated with the polynucleotide. In some embodiments, the isolated nucleic acid molecule, the isolated nucleotide sequence, the isolated peptide, the isolated amino acid sequence, and/or the isolated polypeptide is at least about 1%, 5%, 10%, 20%, 30%, 40%, 50%, 60%, 70%, 80%, 90%, 95%, or more pure.

In other embodiments, an isolated nucleic acid molecule, nucleotide sequence or polypeptide may exist in a non-native environment such as, for example, a recombinant host cell. Thus, for example, with respect to nucleotide sequences, the term "isolated" means that it is separated from the chromosome and/or cell in which it naturally occurs. A polynucleotide is also isolated if it is separated from the chromosome and/or cell in which it naturally occurs in and is then inserted into a genetic context, a chromosome and/or a cell in which it does not naturally occur (e.g., a different host cell, different regulatory sequences, and/or different position in the genome than as found in nature). Accordingly, the recombinant nucleic acid molecules, nucleotide sequences and their encoded polypeptides are "isolated" in that, by the hand of man, they exist apart from their native environment and therefore are not products of nature, however, in some embodiments, they can be introduced into and exist in a recombinant host cell.

As used herein "sequence identity" refers to the extent to which two optimally aligned polynucleotide or peptide sequences are invariant throughout a window of alignment of components, e.g., nucleotides or amino acids. "Identity" can be readily calculated by The Basic Local Alignment Search Tool (BLAST™) available from the National Center for Biotechnology Information of the National Institutes of Health, at https://blast.ncbi.nlm.nih.gov/Blast.cgi.

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned. In some embodiments, "percent identity" can refer to the percentage of identical amino acids in an amino acid sequence.

As used herein, the phrase "substantially identical," in the context of two nucleic acid molecules, nucleotide sequences, or polypeptide sequences, refers to two or more sequences or subsequences that have at least about 80%, least about 85%, at least about 90%, at least about 95%, at least about 96%, at least about 97%, at least about 98%, or at least about 99% nucleotide or amino acid residue identity, when compared and aligned for maximum correspondence, as measured using one of the following sequence comparison algorithms or by visual inspection. For sequence comparison, typically one sequence acts as a reference sequence to which test sequences are compared. When using a sequence comparison algorithm, test and reference sequences are entered into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

The percent of sequence identity can be determined using the "Gap" program of the Sequence Analysis Software Package™ (Version 10; Genetics Computer Group, Inc., Madison, Wis.). "Gap" utilizes the algorithm of Needleman and Wunsch (Needleman and Wunsch, JMol. Biol. 48:443-453, 1970) to find the alignment of two sequences that maximizes the number of matches and minimizes the number of gaps.

As is apparent from the foregoing general description and the specific embodiments, while forms of the embodiments have been illustrated and described, various modifications can be made without departing from the spirit and scope of the present disclosure. Accordingly, it is not intended that the present disclosure be limited thereby. Likewise, the term "comprising" is considered synonymous with the term "including." Likewise whenever a composition, an element or a group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa, e.g., the terms "comprising," "consisting essentially of," "consisting of" also include the product of the combinations of elements listed after the term.

Furthermore, although embodiments disclosed herein may achieve advantages over other possible solutions or over the prior art, whether or not a particular advantage is achieved by a given embodiment is not limiting of the scope of the present disclosure. Thus, the aspects, features, embodiments, and advantages described are merely illustrative and are not considered elements or limitations of the appended claims except where explicitly recited in a claim(s). Likewise, reference to "the disclosure" shall not be construed as a generalization of any inventive subject matter disclosed herein and shall not be considered to be an element or limitation of the appended claims except where explicitly recited in a claim(s).

As used herein, a "composition" can include component(s) of the composition and/or reaction product(s) of two or more components of the composition. Compositions of the present disclosure can be prepared by any suitable mixing process.

References cited herein are incorporated by reference herein in their entirety to indicate the state of the art as of their publication or filing date and it is intended that this information can be employed herein, if needed, to exclude specific embodiments that are in the prior art.

For purposes of this present disclosure, and unless otherwise specified, all numerical values within the detailed description and the claims herein are modified by "about" or "approximately" the indicated value, and consider experimental error and variations that would be expected by a person having ordinary skill in the art. For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, within a range includes every point or individual value between its end points even though not explicitly recited. Thus, every point or individual value may serve as its own lower or upper limit combined with any other point or individual value or any other lower or upper limit, to recite a range not explicitly recited.

As used herein, the indefinite article "a" or "an" shall mean "at least one" unless specified to the contrary or the context clearly indicates otherwise. For example, embodiments comprising "an IDP" include embodiments comprising one, two, or more IDPs, or at least one IDP, unless specified to the contrary or the context clearly indicates only one IDP is included.

While the foregoing is directed to embodiments of the present disclosure, other and further aspects of the disclosure may be devised without departing from the basic scope thereof, and the scope thereof is determined by the claims that follow.

What is claimed is:

1. A composition comprising:
   a first component comprising at least one intrinsically disordered protein comprising the amino acid sequence of SEQ ID NO: 28 or 32; and
   a second component comprising at least one biological material of interest, at least one biologically-derived material of interest, or both, the second component being free of the at least one intrinsically disordered protein.

2. The composition of claim 1, wherein the at least one biological material of interest, the at least one biologically-derived material of interest, or both, comprises a peptide, a polypeptide, a nucleic acid, a nucleotide, a lipid, a polylipid, a saccharide, a polysaccharide, derivatives thereof, or combinations thereof.

3. The composition of claim 1, wherein the at least one biological material of interest, the at least one biologically-derived material of interest, or both, comprises a nucleic acid, a nucleotide, a lipid, a polylipid, derivatives thereof, or combinations thereof.

4. The composition of claim 1, wherein the composition is a liquid.

5. The composition of claim 1, wherein the composition is a solid.

6. The composition of claim 1, wherein the at least one biological material of interest, the at least one biologically-derived material of interest, or both, comprises a protein-based vaccine, an antibody, an enzyme, a hormone, a globular protein, or combinations thereof.

7. The composition of claim 1, wherein the at least one biological material of interest, the at least one biologically-derived material of interest, or both, is part of a food.

8. The composition of claim 1, wherein the at least one biological material of interest, the at least one biologically-derived material of interest, or both, comprises a therapeutic agent, a diagnostic agent, or a combination thereof.

9. The composition of claim 8, wherein the therapeutic agent comprises a nucleic acid-based vaccine, nucleic acid-based gene therapy, a lipid-based nanoparticle, lipid-based therapeutic, or combinations thereof.

10. A method of stabilizing at least one biological material of interest, at least one biologically-derived material of interest, or both, comprising:
mixing a first solution comprising at least one intrinsically disordered protein comprising the amino acid sequence of SEQ ID NO:28 or 32 with a second component comprising at least one biological material of interest, at least one biologically-derived material of interest, or both, to form a liquid composition,
wherein the second component is free of the at least one intrinsically disordered protein.

11. The method of claim 10, further comprising:
at least partially drying the liquid composition to form a solid composition, the solid composition comprising:
the at least one intrinsically disordered protein; and
the at least one biological material of interest, the at least one biologically-derived material of interest, or both.

12. The method of claim 10, wherein the at least one biological material of interest, the at least one biologically-derived material of interest, or both, comprises a peptide, a polypeptide, a nucleic acid, a nucleotide, a lipid, a polylipid, a saccharide, a polysaccharide, derivatives thereof, or combinations thereof.

13. The method of claim 10, wherein the at least one biological material of interest, the at least one biologically-derived material of interest, or both, comprises a nucleic acid, a nucleotide, a lipid, a polylipid, derivatives thereof, or combinations thereof.

14. The method of claim 10, wherein the at least one biological material of interest, the at least one biologically-derived material of interest, or both, comprises a protein-based vaccine, an antibody, an enzyme, a hormone, a globular protein, or combinations thereof.

15. The method of claim 10, wherein the at least one biological material of interest, the at least one biologically-derived material of interest, or both, comprises a therapeutic agent, a diagnostic agent, or a combination thereof.

16. The method of claim 15, wherein the therapeutic agent comprises a nucleic acid-based vaccine, nucleic acid-based gene therapy, a lipid-based nanoparticle, lipid-based therapeutic, or combinations thereof.

17. The method of claim 10, wherein the at least one biological material of interest, the at least one biologically-derived material of interest, or both, is part of a food.

18. A recombinant nucleic acid construct selected from the group consisting of:
(a) a nucleotide sequence of SEQ ID NO: 27, or 31, or a complement thereof;
(b) a nucleotide sequence that encodes a polypeptide comprising an amino acid sequence of SEQ ID NO: 28, or 32, or a complement thereof;
(c) a nucleotide sequence which anneals under stringent hybridization conditions to the nucleotide sequence of any one of (a) to (b), or a complement thereof;
(d) a nucleotide sequence that differs from the nucleotide sequences of any one of (a) to (c) above due to the degeneracy of the genetic code;
(e) any combination of the nucleotide sequences of (a)-(d).

* * * * *

SEQUENCE LISTING

<160> NUMBER OF SEQ ID NOS: 32

<210> SEQ ID NO 1
<211> LENGTH: 273
<212> TYPE: DNA
<213> ORGANISM: Unknown
<220> FEATURE:
<223> OTHER INFORMATION: Tardigrade (WT CAHS D Protein) (DNA)

<400> SEQUENCE: 1

```
atgtcagggc gtaacgtgga gtcccatatg gagcgcaacg aaaaagtggt agtgaataac     60
tccggtcatg cggacgtgaa aaaacagcaa caacaggttg aacatacgga gttcacgcat    120
acagaagtaa agccccgct catccaccca gcccctccga ttatttcgac tggcgccgcg    180
ggcttagcgg aggaaattgt gggccagggt tttactgcgt cagcagcgcg tatctcaggt    240
ggcactgccg aagtgcatct gcagccgtca taa                                  273
```

<210> SEQ ID NO 2
<211> LENGTH: 90
<212> TYPE: PRT
<213> ORGANISM: Unknown
<220> FEATURE:
<223> OTHER INFORMATION: Tardigrade (WT CAHS D Protein) (Protein)

<400> SEQUENCE: 2

```
Met Ser Gly Arg Asn Val Glu Ser His Met Glu Arg Asn Glu Lys Val
1               5                  10                  15
Val Val Asn Asn Ser Gly His Ala Asp Val Lys Lys Gln Gln Gln Gln
            20                  25                  30
Val Glu His Thr Glu Phe Thr His Thr Glu Val Lys Ala Pro Leu Ile
        35                  40                  45
His Pro Ala Pro Pro Ile Ile Ser Thr Gly Ala Ala Gly Leu Ala Glu
    50                  55                  60
Glu Ile Val Gly Gln Gly Phe Thr Ala Ser Ala Ala Arg Ile Ser Gly
65                  70                  75                  80
Gly Thr Ala Glu Val His Leu Gln Pro Ser
                85                  90
```

<210> SEQ ID NO 3
<211> LENGTH: 273
<212> TYPE: DNA
<213> ORGANISM: Artificial
<220> FEATURE:
<223> OTHER INFORMATION: Modified Tardigrade CAHS Protein (Mutant N CAHS
      Protein, No C Teminus or Linker Region) (DNA)

<400> SEQUENCE: 3

```
atgtcagggc gtaacgtgga gtcccatatg gagcgcaacg aaaaagtggt agtgaataac     60
tccggtcatg cggacgtgaa aaaacagcaa caacaggttg aacatacgga gttcacgcat    120
acagaagtaa agccccgct catccaccca gcccctccga ttatttcgac tggcgccgcg    180
ggcttagcgg aggaaattgt gggccagggt tttactgcgt cagcagcgcg tatctcaggt    240
ggcactgccg aagtgcatct gcagccgtca taa                                  273
```

<210> SEQ ID NO 4
<211> LENGTH: 90
<212> TYPE: PRT
<213> ORGANISM: Artificial
<220> FEATURE:
<223> OTHER INFORMATION: Modified Tardigrade CAHS Protein (Mutant N CAHS
      Protein, No C Teminus or Linker Region) (Protein)

<400> SEQUENCE: 4

Met Ser Gly Arg Asn Val Glu Ser His Met Glu Arg Asn Glu Lys Val
1               5                   10                  15

Val Val Asn Asn Ser Gly His Ala Asp Val Lys Lys Gln Gln Gln Gln
            20                  25                  30

Val Glu His Thr Glu Phe Thr His Thr Glu Val Lys Ala Pro Leu Ile
        35                  40                  45

His Pro Ala Pro Pro Ile Ile Ser Thr Gly Ala Ala Gly Leu Ala Glu
    50                  55                  60

Glu Ile Val Gly Gln Gly Phe Thr Ala Ser Ala Ala Arg Ile Ser Gly
65                  70                  75                  80

Gly Thr Ala Glu Val His Leu Gln Pro Ser
                85                  90

<210> SEQ ID NO 5
<211> LENGTH: 330
<212> TYPE: DNA
<213> ORGANISM: Artificial
<220> FEATURE:
<223> OTHER INFORMATION: Modified Tardigrade CAHS Protein (Mutant Linker
      CAHS Protein, No C Teminus or N Terminus) (DNA)

<400> SEQUENCE: 5
atgggcagca gcgcggcgat gacagaagaa gctcgccgtg atcaggaacg ttatcggcag     60
gagcaggaaa gtattgcgaa acaacaggaa cgggaaatgg aaaagaagac cgaagcgtac    120
cgcaagacgg cggaggcgga agctgaaaaa attcgtaaag aactggaaaa acaacatgcg    180
cgcgatgtcg aattccgtaa agatctgatc gaatccacga tcgatcgtca gaaacgtgaa    240
gtggatctgg aagcgaaaat ggctaaacgc gagttagatc gtgaaggtca gctggctaaa    300
gaagccctgg aacgctctcg gttagcctaa                                    330

<210> SEQ ID NO 6
<211> LENGTH: 109
<212> TYPE: PRT
<213> ORGANISM: Artificial
<220> FEATURE:
<223> OTHER INFORMATION: Modified Tardigrade CAHS Protein (Mutant Linker
      CAHS Protein, No C Teminus or N Terminus) (Protein)

<400> SEQUENCE: 6

Met Gly Ser Ser Ala Ala Met Thr Glu Glu Ala Arg Arg Asp Gln Glu
1               5                   10                  15

Arg Tyr Arg Gln Glu Gln Glu Ser Ile Ala Lys Gln Gln Glu Arg Glu
            20                  25                  30

Met Glu Lys Lys Thr Glu Ala Tyr Arg Lys Thr Ala Glu Ala Glu Ala
        35                  40                  45

Glu Lys Ile Arg Lys Glu Leu Glu Lys Gln His Ala Arg Asp Val Glu
    50                  55                  60

Phe Arg Lys Asp Leu Ile Glu Ser Thr Ile Asp Arg Gln Lys Arg Glu
65                  70                  75                  80

Val Asp Leu Glu Ala Lys Met Ala Lys Arg Glu Leu Asp Arg Glu Gly
                85                  90                  95

Gln Leu Ala Lys Glu Ala Leu Glu Arg Ser Arg Leu Ala
            100                 105

<210> SEQ ID NO 7
<211> LENGTH: 111

<212> TYPE: DNA
<213> ORGANISM: Artificial
<220> FEATURE:
<223> OTHER INFORMATION: Modified Tardigrade CAHS Protein (Mutant C CAHS
      Protein, No N Teminus or Linker Region) (DNA)

<400> SEQUENCE: 7
atgggcagca gcacgaacgt cgaagttaac ttcgattcgg cagccgggca tacagtcagt    60
ggagggacca ctgttagcac tagcgataag atggaaatta aacgcaacta a            111

<210> SEQ ID NO 8
<211> LENGTH: 36
<212> TYPE: PRT
<213> ORGANISM: Artificial
<220> FEATURE:
<223> OTHER INFORMATION: Modified Tardigrade CAHS Protein (Mutant C CAHS
      Protein, No N Teminus or Linker Region) (Protein)

<400> SEQUENCE: 8

Met Gly Ser Ser Thr Asn Val Glu Val Asn Phe Asp Ser Ala Ala Gly
1               5                   10                  15

His Thr Val Ser Gly Gly Thr Thr Val Ser Thr Ser Asp Lys Met Glu
            20                  25                  30

Ile Lys Arg Asn
        35

<210> SEQ ID NO 9
<211> LENGTH: 345
<212> TYPE: DNA
<213> ORGANISM: Artificial
<220> FEATURE:
<223> OTHER INFORMATION: Modified Tardigrade CAHS Protein (Mutant NL1
      CAHS Protein, No C Teminus and Partial Linker Region) (DNA)

<400> SEQUENCE: 9
atgtcagggc gtaacgtgga gtcccatatg gagcgcaacg aaaaagtggt agtgaataac    60
tccggtcatg cggacgtgaa aaaacagcaa caacaggttg aacatacgga gttcacgcat   120
acagaagtaa agcccccgct catccaccca gcccctccga ttatttcgac tggcgccgcg   180
ggcttagcgg aggaaattgt gggccagggt tttactgcgt cagcagcgcg tatctcaggt   240
ggcactgccg aagtgcatct gcagccgtca gcggcgatga cagaagaagc tcgccgtgat   300
caggaacgtt atcggcagga gcaggaaagt attgcgaaac aataa                   345

<210> SEQ ID NO 10
<211> LENGTH: 114
<212> TYPE: PRT
<213> ORGANISM: Artificial
<220> FEATURE:
<223> OTHER INFORMATION: Modified Tardigrade CAHS Protein (Mutant NL1
      CAHS Protein, No C Teminus and Partial Linker Region) (Protein)

<400> SEQUENCE: 10

Met Ser Gly Arg Asn Val Glu Ser His Met Glu Arg Asn Glu Lys Val
1               5                   10                  15

Val Val Asn Asn Ser Gly His Ala Asp Val Lys Lys Gln Gln Gln Gln
            20                  25                  30

Val Glu His Thr Glu Phe Thr His Thr Glu Val Lys Ala Pro Leu Ile
        35                  40                  45

His Pro Ala Pro Pro Ile Ile Ser Thr Gly Ala Ala Gly Leu Ala Glu
    50                  55                  60

Glu Ile Val Gly Gln Gly Phe Thr Ala Ser Ala Ala Arg Ile Ser Gly
65                  70                  75                  80

Gly Thr Ala Glu Val His Leu Gln Pro Ser Ala Ala Met Thr Glu Glu
                85                  90                  95

Ala Arg Arg Asp Gln Glu Arg Tyr Arg Gln Glu Gln Glu Ser Ile Ala
            100                 105                 110

Lys Gln

<210> SEQ ID NO 11
<211> LENGTH: 345
<212> TYPE: DNA
<213> ORGANISM: Artificial
<220> FEATURE:
<223> OTHER INFORMATION: Modified Tardigrade CAHS Protein (Mutant CL1
      CAHS Protein, No N Teminus and Partial Linker Region) (DNA)

<400> SEQUENCE: 11
atgcaggaac gggaaatgga aaagaagacc gaagcgtacc gcaagacggc ggaggcggaa      60
gctgaaaaaa ttcgtaaaga actggaaaaa caacatgcgc gcgatgtcga attccgtaaa     120
gatctgatcg aatccacgat cgatcgtcag aaacgtgaag tggatctgga agcgaaaatg     180
gctaaacgcg agttagatcg tgaaggtcag ctggctaaag aagccctgga acgctctcgg     240
ttagccacga acgtcgaagt taacttcgat tcggcagccg gcatacagt cagtggaggg      300 accactgtta gcactagcga taagatggaa attaaacgca actaa                     345

<210> SEQ ID NO 12
<211> LENGTH: 114
<212> TYPE: PRT
<213> ORGANISM: Artificial
<220> FEATURE:
<223> OTHER INFORMATION: Modified Tardigrade CAHS Protein (Mutant CL1
      CAHS Protein, No N Teminus and Partial Linker Region) (Protein)

<400> SEQUENCE: 12

Met Gln Glu Arg Glu Met Glu Lys Lys Thr Glu Ala Tyr Arg Lys Thr
1               5                   10                  15

Ala Glu Ala Glu Ala Glu Lys Ile Arg Lys Glu Leu Glu Lys Gln His
            20                  25                  30

Ala Arg Asp Val Glu Phe Arg Lys Asp Leu Ile Glu Ser Thr Ile Asp
        35                  40                  45

Arg Gln Lys Arg Glu Val Asp Leu Glu Ala Lys Met Ala Lys Arg Glu
    50                  55                  60

Leu Asp Arg Glu Gly Gln Leu Ala Lys Glu Ala Leu Glu Arg Ser Arg
65                  70                  75                  80

Leu Ala Thr Asn Val Glu Val Asn Phe Asp Ser Ala Ala Gly His Thr
                85                  90                  95

Val Ser Gly Gly Thr Thr Val Ser Thr Ser Asp Lys Met Glu Ile Lys
            100                 105                 110

Arg Asn

<210> SEQ ID NO 13
<211> LENGTH: 441
<212> TYPE: DNA
<213> ORGANISM: Artificial
<220> FEATURE:
<223> OTHER INFORMATION: Modified Tardigrade CAHS Protein (Mutant 0.5x
      Linker CAHS Protein, Partial Linker Region) (DNA)

<400> SEQUENCE: 13

```
atgtcagggc gtaacgtgga gtcccatatg gagcgcaacg aaaaagtggt agtgaataac    60
tccggtcatg cggacgtgaa aaaacagcaa caacaggttg aacatacgga gttcacgcat   120
acagaagtaa aagccccgct catccaccca gcccctccga ttatttcgac tggcgccgcg   180
ggcttagcgg aggaaattgt gggccagggt tttactgcgt cagcagcgcg tatctcaggt   240
ggcactgccg aagtgcatct gcagccgtca gcggcgatga cagaagaagc tcgccgtgat   300
caggaacgtt atcggcagga gcaggaaagt attgcgaaac aaacgaacgt cgaagttaac   360
ttcgattcgg cagccgggca tacagtcagt ggagggacca ctgttagcac tagcgataag   420
atggaaatta aacgcaacta a                                             441
```

<210> SEQ ID NO 14
<211> LENGTH: 146
<212> TYPE: PRT
<213> ORGANISM: Artificial
<220> FEATURE:
<223> OTHER INFORMATION: Modified Tardigrade CAHS Protein (Mutant 0.5x
      Linker CAHS Protein, Partial Linker Region) (Protein)

<400> SEQUENCE: 14

```
Met Ser Gly Arg Asn Val Glu Ser His Met Glu Arg Asn Glu Lys Val
1               5                   10                  15

Val Val Asn Asn Ser Gly His Ala Asp Val Lys Lys Gln Gln Gln Gln
            20                  25                  30

Val Glu His Thr Glu Phe Thr His Thr Glu Val Lys Ala Pro Leu Ile
        35                  40                  45

His Pro Ala Pro Pro Ile Ile Ser Thr Gly Ala Ala Gly Leu Ala Glu
    50                  55                  60

Glu Ile Val Gly Gln Gly Phe Thr Ala Ser Ala Ala Arg Ile Ser Gly
65                  70                  75                  80

Gly Thr Ala Glu Val His Leu Gln Pro Ser Ala Ala Met Thr Glu Glu
                85                  90                  95

Ala Arg Arg Asp Gln Glu Arg Tyr Arg Gln Glu Gln Glu Ser Ile Ala
            100                 105                 110

Lys Gln Thr Asn Val Glu Val Asn Phe Asp Ser Ala Ala Gly His Thr
        115                 120                 125

Val Ser Gly Gly Thr Thr Val Ser Thr Ser Asp Lys Met Glu Ile Lys
    130                 135                 140

Arg Asn
145
```

<210> SEQ ID NO 15
<211> LENGTH: 684
<212> TYPE: DNA
<213> ORGANISM: Unknown
<220> FEATURE:
<223> OTHER INFORMATION: Tardigrade (WT CAHS D Protein) (DNA)

<400> SEQUENCE: 15

```
atgtcagggc gtaacgtgga gtcccatatg gagcgcaacg aaaaagtggt agtgaataac    60
tccggtcatg cggacgtgaa aaaacagcaa caacaggttg aacatacgga gttcacgcat   120
acagaagtaa aagccccgct catccaccca gcccctccga ttatttcgac tggcgccgcg   180
ggcttagcgg aggaaattgt gggccagggt tttactgcgt cagcagcgcg tatctcaggt   240
ggcactgccg aagtgcatct gcagccgtca gcggcgatga cagaagaagc tcgccgtgat   300
```

```
caggaacgtt atcggcagga gcaggaaagt attgcgaaac aacaggaacg ggaaatggaa    360
aagaagaccg aagcgtaccg caagacggcg gaggcggaag ctgaaaaaat tcgtaaagaa    420
ctggaaaaac aacatgcgcg cgatgtcgaa ttccgtaaag atctgatcga atccacgatc    480
gatcgtcaga acgtgaagt ggatctggaa gcgaaatgg ctaaacgcga gttagatcgt     540
gaaggtcagc tggctaaaga agccctggaa cgctctcggt tagccacgaa cgtcgaagtt    600
aacttcgatt cggcagccgg gcatacagtc agtggaggga ccactgttag cactagcgat    660
aagatggaaa ttaaacgcaa ctaa                                            684
```

<210> SEQ ID NO 16
<211> LENGTH: 227
<212> TYPE: PRT
<213> ORGANISM: Unknown
<220> FEATURE:
<223> OTHER INFORMATION: Tardigrade (WT CAHS D Protein) (Protein)

<400> SEQUENCE: 16

```
Met Ser Gly Arg Asn Val Glu Ser His Met Glu Arg Asn Glu Lys Val
1               5                   10                  15

Val Val Asn Asn Ser Gly His Ala Asp Val Lys Lys Gln Gln Gln Gln
            20                  25                  30

Val Glu His Thr Glu Phe Thr His Thr Glu Val Lys Ala Pro Leu Ile
        35                  40                  45

His Pro Ala Pro Pro Ile Ile Ser Thr Gly Ala Ala Gly Leu Ala Glu
    50                  55                  60

Glu Ile Val Gly Gln Gly Phe Thr Ala Ser Ala Ala Arg Ile Ser Gly
65                  70                  75                  80

Gly Thr Ala Glu Val His Leu Gln Pro Ser Ala Ala Met Thr Glu Glu
                85                  90                  95

Ala Arg Arg Asp Gln Glu Arg Tyr Arg Gln Glu Gln Glu Ser Ile Ala
            100                 105                 110

Lys Gln Gln Glu Arg Glu Met Glu Lys Lys Thr Glu Ala Tyr Arg Lys
        115                 120                 125

Thr Ala Glu Ala Glu Ala Glu Lys Ile Arg Lys Glu Leu Glu Lys Gln
    130                 135                 140

His Ala Arg Asp Val Glu Phe Arg Lys Asp Leu Ile Glu Ser Thr Ile
145                 150                 155                 160

Asp Arg Gln Lys Arg Glu Val Asp Leu Glu Ala Lys Met Ala Lys Arg
                165                 170                 175

Glu Leu Asp Arg Glu Gly Gln Leu Ala Lys Glu Ala Leu Glu Arg Ser
            180                 185                 190

Arg Leu Ala Thr Asn Val Glu Val Asn Phe Asp Ser Ala Ala Gly His
        195                 200                 205

Thr Val Ser Gly Gly Thr Thr Val Ser Thr Ser Asp Lys Met Glu Ile
    210                 215                 220

Lys Arg Asn
225
```

<210> SEQ ID NO 17
<211> LENGTH: 315
<212> TYPE: DNA
<213> ORGANISM: Artificial
<220> FEATURE:
<223> OTHER INFORMATION: Modified Tardigrade CAHS Protein (Mutant Linker
      CAHS Protein, No C Teminus or N Terminus) (DNA)

<400> SEQUENCE: 17

```
gcagctatga cggaagaggc acgccgtgat caagagcgct accgtcaaga gcaagaaagt    60
attgccaaac aacaggagcg cgagatggaa aaaaaaactg aggcataccg taagacggca   120
gaagccgaag cagagaagat tcgcaaagag ctggagaaac aacatgcccg tgacgtagaa   180
tttcgcaagg atttgatcga gtcaaccatc gaccgccaga acgcgaggt ggaccttgag    240 gctaagatgg ctaaacgtga gcttgatcgc gaaggccaac tggcgaaaga ggcgctggaa   300
cgctctcggt tagcc                                                   315
```

<210> SEQ ID NO 18
<211> LENGTH: 105
<212> TYPE: PRT
<213> ORGANISM: Artificial
<220> FEATURE:
<223> OTHER INFORMATION: Modified Tardigrade CAHS Protein (Mutant Linker CAHS Protein, No C Teminus or N Terminus) (Protein)

<400> SEQUENCE: 18

```
Ala Ala Met Thr Glu Glu Ala Arg Arg Asp Gln Glu Arg Tyr Arg Gln
 1               5                  10                  15

Glu Gln Glu Ser Ile Ala Lys Gln Gln Glu Arg Glu Met Glu Lys Lys
            20                  25                  30

Thr Glu Ala Tyr Arg Lys Thr Ala Glu Ala Glu Ala Glu Lys Ile Arg
        35                  40                  45

Lys Glu Leu Glu Lys Gln His Ala Arg Asp Val Glu Phe Arg Lys Asp
    50                  55                  60

Leu Ile Glu Ser Thr Ile Asp Arg Gln Lys Arg Glu Val Asp Leu Glu
65                  70                  75                  80

Ala Lys Met Ala Lys Arg Glu Leu Asp Arg Glu Gly Gln Leu Ala Lys
                85                  90                  95

Glu Ala Leu Glu Arg Ser Arg Leu Ala
            100                 105
```

<210> SEQ ID NO 19
<211> LENGTH: 858
<212> TYPE: DNA
<213> ORGANISM: Artificial
<220> FEATURE:
<223> OTHER INFORMATION: Modified Tardigrade CAHS Protein (Mutant NLN CAHS Protein, Two N-termini Connected By Linker) (DNA)

<400> SEQUENCE: 19

```
atgtcagggc gtaacgtgga gtcccatatg gagcgcaacg aaaaagtggt agtgaataac    60
tccggtcatg cggacgtgaa aaaacagcaa caacaggttg aacatacgga gttcacgcat   120
acagaagtaa agcccccgct catccaccca gcccctccga ttatttcgac tggcgccgcg   180
ggcttagcgg aggaaattgt gggccagggt tttactgcgt cagcagcgcg tatctcaggt   240
ggcactgccg aagtgcatct gcagccgtca gcggcgatga cagaagaagc tcgccgtgat   300
caggaacgtt atcggcagga gcaggaaagt attgcgaaac aacaggaacg ggaaatggaa   360
aagaagaccg aagcgtaccg caagacggcg gaggcggaag ctgaaaaaat tcgtaaagaa   420
ctggaaaaac aacatgcgcg cgatgtcgaa ttccgtaaag atctgatcga atccacgatc   480
gatcgtcaga acgtgaagt ggatctggaa gcgaaaatgg ctaaacgcga gttagatcgt   540
gaaggtcagc tggctaaaga agccctggaa cgctctcggt tagccatgtc aggtaggaat   600
gtcgagtctc acatggaacg caacgagaag gtagtcgtga caactcagg acacgcagac   660
```

```
gtcaagaagc agcagcagca ggtcgaacac acagagttca ctcataccga ggtgaaagct    720
ccgctgatcc atcctgctcc cccaatcata agcacaggag ccgctggcct ggcagaagaa    780
atagtgggcc agggttttac agcaagtgcc gctaggataa gcggaggaac cgctgaagtg    840
catctccagc cctcctaa                                                  858
```

<210> SEQ ID NO 20
<211> LENGTH: 285
<212> TYPE: PRT
<213> ORGANISM: Artificial
<220> FEATURE:
<223> OTHER INFORMATION: Modified Tardigrade CAHS Protein (Mutant NLN
      CAHS Protein, Two N-termini Connected By Linker) (Protein)

<400> SEQUENCE: 20

```
Met Ser Gly Arg Asn Val Glu Ser His Met Glu Arg Asn Glu Lys Val
1               5                   10                  15

Val Val Asn Asn Ser Gly His Ala Asp Val Lys Lys Gln Gln Gln Gln
            20                  25                  30

Val Glu His Thr Glu Phe Thr His Thr Glu Val Lys Ala Pro Leu Ile
        35                  40                  45

His Pro Ala Pro Ile Ile Ser Thr Gly Ala Ala Gly Leu Ala Glu
    50                  55                  60

Glu Ile Val Gly Gln Gly Phe Thr Ala Ser Ala Ala Arg Ile Ser Gly
65                  70                  75                  80

Gly Thr Ala Glu Val His Leu Gln Pro Ser Ala Ala Met Thr Glu Glu
                85                  90                  95

Ala Arg Arg Asp Gln Glu Arg Tyr Arg Gln Gln Glu Ser Ile Ala
            100                 105                 110

Lys Gln Gln Glu Arg Glu Met Glu Lys Lys Thr Glu Ala Tyr Arg Lys
        115                 120                 125

Thr Ala Glu Ala Glu Ala Glu Lys Ile Arg Lys Glu Leu Glu Lys Gln
    130                 135                 140

His Ala Arg Asp Val Glu Phe Arg Lys Asp Leu Ile Glu Ser Thr Ile
145                 150                 155                 160

Asp Arg Gln Lys Arg Glu Val Asp Leu Glu Ala Lys Met Ala Lys Arg
                165                 170                 175

Glu Leu Asp Arg Glu Gly Gln Leu Ala Lys Glu Ala Leu Glu Arg Ser
            180                 185                 190

Arg Leu Ala Met Ser Gly Arg Asn Val Glu Ser His Met Glu Arg Asn
        195                 200                 205

Glu Lys Val Val Val Asn Asn Ser Gly His Ala Asp Val Lys Lys Gln
    210                 215                 220

Gln Gln Gln Val Glu His Thr Glu Phe Thr His Thr Glu Val Lys Ala
225                 230                 235                 240

Pro Leu Ile His Pro Ala Pro Ile Ile Ser Thr Gly Ala Ala Gly
                245                 250                 255

Leu Ala Glu Glu Ile Val Gly Gln Gly Phe Thr Ala Ser Ala Ala Arg
            260                 265                 270

Ile Ser Gly Gly Thr Ala Glu Val His Leu Gln Pro Ser
        275                 280                 285
```

<210> SEQ ID NO 21
<211> LENGTH: 513
<212> TYPE: DNA
<213> ORGANISM: Artificial
<220> FEATURE:

<223> OTHER INFORMATION: Modified Tardigrade CAHS Protein (Mutant CLC
CAHS Protein, Two C-termini Connected By Linker) (DNA)

<400> SEQUENCE: 21

```
atgaccaacg tcgaagtgaa tttcgactct gcggctggtc acacggtatc cggcggcact      60
accgtgagca catccgataa aatggaaatc aagcgtaatg cagcgatgac ggaagaggct     120
cgtcgcgacc aagaacgcta ccgccaagaa caggaaagca tcgccaagca acaggagcgt     180
gaaatggaaa agaaaaccga ggcttaccgt aaaactgcgg aagctgaggc cgaaaaaatc     240
cgtaaggaat tagaaaaaca cacgcgcgc gacgtggagt ttcgtaaaga ccttatcgaa      300
agtactattg accgtcaaaa acgtgaagtt gatttagaag cgaagatggc gaagcgcgag     360
ctggaccgtg aaggacagct ggctaaggag gcgttggagc gttcccgctt ggccactaat     420
gttgaagtaa attttgattc cgccgccggt cacacagttt ccggcggaac aacagtgtca     480
acttcggata aaatggagat caaacgcaat taa                                  513
```

<210> SEQ ID NO 22
<211> LENGTH: 170
<212> TYPE: PRT
<213> ORGANISM: Artificial
<220> FEATURE:
<223> OTHER INFORMATION: Modified Tardigrade CAHS Protein (Mutant CLC
CAHS Protein, Two C-termini Connected By Linker) (Protein)

<400> SEQUENCE: 22

```
Met Thr Asn Val Glu Val Asn Phe Asp Ser Ala Gly His Thr Val
1               5                   10                  15

Ser Gly Gly Thr Thr Val Ser Thr Ser Asp Lys Met Glu Ile Lys Arg
            20                  25                  30

Asn Ala Ala Met Thr Glu Glu Ala Arg Arg Asp Gln Glu Arg Tyr Arg
        35                  40                  45

Gln Glu Gln Glu Ser Ile Ala Lys Gln Gln Glu Arg Glu Met Glu Lys
    50                  55                  60

Lys Thr Glu Ala Tyr Arg Lys Thr Ala Glu Ala Glu Ala Glu Lys Ile
65                  70                  75                  80

Arg Lys Glu Leu Glu Lys Gln His Ala Arg Asp Val Glu Phe Arg Lys
                85                  90                  95

Asp Leu Ile Glu Ser Thr Ile Asp Arg Gln Lys Arg Glu Val Asp Leu
            100                 105                 110

Glu Ala Lys Met Ala Lys Arg Glu Leu Asp Arg Glu Gly Gln Leu Ala
        115                 120                 125

Lys Glu Ala Leu Glu Arg Ser Arg Leu Ala Thr Asn Val Glu Val Asn
    130                 135                 140

Phe Asp Ser Ala Ala Gly His Thr Val Ser Gly Gly Thr Thr Val Ser
145                 150                 155                 160

Thr Ser Asp Lys Met Glu Ile Lys Arg Asn
                165                 170
```

<210> SEQ ID NO 23
<211> LENGTH: 345
<212> TYPE: DNA
<213> ORGANISM: Artificial
<220> FEATURE:
<223> OTHER INFORMATION: Modified Tardigrade CAHS Protein (Mutant CL2
CAHS Protein, No N Teminus and Partial Linker Region) (DNA)

<400> SEQUENCE: 23

```
atgcaggaac gggaaatgga aaagaagacc gaagcgtacc gcaagacggc ggaggcggaa    60
gctgaaaaaa ttcgtaaaga actggaaaaa caacatgcgc gcgatgtcga attccgtaaa   120
gatctgatcg aatccacgat cgatcgtcag aaacgtgaag tggatctgga agcgaaaatg   180
gctaaacgcg agttagatcg tgaaggtcag ctggctaaag aagccctgga acgctctcgg   240
ttagccacga acgtcgaagt taacttcgat tcggcagccg gcatacagt cagtggaggg    300
accactgtta gcactagcga taagatggaa attaaacgca actaa                   345
```

<210> SEQ ID NO 24
<211> LENGTH: 114
<212> TYPE: PRT
<213> ORGANISM: Artificial
<220> FEATURE:
<223> OTHER INFORMATION: Modified Tardigrade CAHS Protein (Mutant CL2
      CAHS Protein, No N Teminus and Partial Linker Region) (Protein)

<400> SEQUENCE: 24

```
Met Gln Glu Arg Glu Met Glu Lys Lys Thr Glu Ala Tyr Arg Lys Thr
1               5                   10                  15
Ala Glu Ala Glu Ala Glu Lys Ile Arg Lys Glu Leu Glu Lys Gln His
            20                  25                  30
Ala Arg Asp Val Glu Phe Arg Lys Asp Leu Ile Glu Ser Thr Ile Asp
        35                  40                  45
Arg Gln Lys Arg Glu Val Asp Leu Glu Ala Lys Met Ala Lys Arg Glu
    50                  55                  60
Leu Asp Arg Glu Gly Gln Leu Ala Lys Glu Ala Leu Glu Arg Ser Arg
65                  70                  75                  80
Leu Ala Thr Asn Val Glu Val Asn Phe Asp Ser Ala Ala Gly His Thr
                85                  90                  95
Val Ser Gly Gly Thr Thr Val Ser Thr Ser Asp Lys Met Glu Ile Lys
            100                 105                 110
Arg Asn
```

<210> SEQ ID NO 25
<211> LENGTH: 345
<212> TYPE: DNA
<213> ORGANISM: Artificial
<220> FEATURE:
<223> OTHER INFORMATION: Modified Tardigrade CAHS Protein (Mutant NL2
      CAHS Protein, No C Teminus and Partial Linker Region) (DNA)

<400> SEQUENCE: 25

```
atgtcagggc gtaacgtgga gtcccatatg gagcgcaacg aaaaagtggt agtgaataac    60
tccggtcatg cggacgtgaa aaacagcaa caacaggttg aacatacgga gttcacgcat   120
acagaagtaa aagccccgct catccaccca gcccctccga ttatttcgac tggcgccgcg   180
ggcttagcgg aggaaattgt gggccagggt tttactgcgt cagcagcgcg tatctcaggt   240
ggcactgccg aagtgcatct gcagccgtca gcggcgatga cagaagaagc tcgccgtgat   300
caggaacgtt atcggcagga gcaggaaagt attgcgaaac aataa                   345
```

<210> SEQ ID NO 26
<211> LENGTH: 114
<212> TYPE: PRT
<213> ORGANISM: Artificial

<220> FEATURE:
<223> OTHER INFORMATION: Modified Tardigrade CAHS Protein (Mutant NL2 CAHS Protein, No C Teminus and Partial Linker Region) (Protein)

<400> SEQUENCE: 26

```
Met Ser Gly Arg Asn Val Glu Ser His Met Glu Arg Asn Glu Lys Val
1               5                   10                  15

Val Val Asn Asn Ser Gly His Ala Asp Val Lys Lys Gln Gln Gln Gln
            20                  25                  30

Val Glu His Thr Glu Phe Thr His Thr Glu Val Lys Ala Pro Leu Ile
        35                  40                  45

His Pro Ala Pro Pro Ile Ile Ser Thr Gly Ala Ala Gly Leu Ala Glu
    50                  55                  60

Glu Ile Val Gly Gln Gly Phe Thr Ala Ser Ala Ala Arg Ile Ser Gly
65                  70                  75                  80

Gly Thr Ala Glu Val His Leu Gln Pro Ser Ala Ala Met Thr Glu Glu
                85                  90                  95

Ala Arg Arg Asp Gln Glu Arg Tyr Arg Gln Gln Glu Ser Ile Ala
            100                 105                 110

Lys Gln
```

<210> SEQ ID NO 27
<211> LENGTH: 999
<212> TYPE: DNA
<213> ORGANISM: Artificial
<220> FEATURE:
<223> OTHER INFORMATION: Modified Tardigrade CAHS Protein (Mutant 2x Linker CAHS Protein) (DNA)

<400> SEQUENCE: 27

```
atgtcagggc gtaacgtgga gtcccatatg gagcgcaacg aaaaagtggt agtgaataac      60
tccggtcatg cggacgtgaa aaaacagcaa caacaggttg aacatacgga gttcacgcat     120
acagaagtaa agcccccgct catccaccca gcccctccga ttatttcgac tggcgccgcg     180
ggcttagcgg aggaaattgt gggccagggt tttactgcgt cagcagcgcg tatctcaggt     240
ggcactgccg aagtgcatct gcagccgtca gcggcgatga cagaagaagc tcgccgtgat     300
caggaacgtt atcggcagga gcaggaaagt attgcgaaac aacaggaacg gaaatggaa      360
aagaagaccg aagcgtaccg caagacggcg gaggcggaag ctgaaaaaat tcgtaaagaa     420
ctggaaaaac aacatgcgcg cgatgtcgaa ttccgtaaag atctgatcga atccacgatc     480
gatcgtcaga acgtgaagt ggatctgaa gcgaaaatgg ctaaacgcga gttagatcgt       540
gaaggtcagc tggctaaaga agccctggaa cgctctcggt tagccacgaa catgacggag     600
gaagcgcgtc gcgatcaaga acgttaccgc aagagcagg agtccatcgc aaaacagcaa     660
gaacgtgaaa tggaaaaaaa gacagaggct taccgtaaga cggcagaagc cgaggccgaa     720
aaaatccgca aggaattgga aaagcagcac gcccgtgatg tagagttccg caaggactta    780
atcgaatcca ccattgatcg ccaaaaacgt gaagtagacc tggaagccaa gatggcgaag    840
cgtgaattgg accgcgaagg ccaattagct aaagaggcgc tggagcgtag tcgcctggcg    900
acgaacgtcg aagttaactt cgattcggca gccgggcata cagtcagtgg agggaccact    960
gttagcacta gcgataagat ggaaattaaa cgcaactaa                             999
```

<210> SEQ ID NO 28
<211> LENGTH: 336
<212> TYPE: PRT
<213> ORGANISM: Artificial

<220> FEATURE:
<223> OTHER INFORMATION: Modified Tardigrade CAHS Protein (Mutant 2x Linker CAHS Protein) (Protein)

<400> SEQUENCE: 28

```
Met Gly Ser Ser Met Ser Gly Arg Asn Val Glu Ser His Met Glu Arg
1               5                   10                  15

Asn Glu Lys Val Val Asn Asn Ser Gly His Ala Asp Val Lys Lys
            20                  25                  30

Gln Gln Gln Val Glu His Thr Glu Phe Thr His Thr Glu Val Lys
        35                  40                  45

Ala Pro Leu Ile His Pro Ala Pro Pro Ile Ile Ser Thr Gly Ala Ala
50                  55                  60

Gly Leu Ala Glu Glu Ile Val Gly Gln Gly Phe Thr Ala Ser Ala Ala
65                  70                  75                  80

Arg Ile Ser Gly Gly Thr Ala Glu Val His Leu Gln Pro Ser Ala Ala
                85                  90                  95

Met Thr Glu Glu Ala Arg Arg Asp Gln Glu Arg Tyr Arg Gln Glu Gln
            100                 105                 110

Glu Ser Ile Ala Lys Gln Gln Glu Arg Glu Met Glu Lys Lys Thr Glu
        115                 120                 125

Ala Tyr Arg Lys Thr Ala Glu Ala Glu Ala Glu Lys Ile Arg Lys Glu
            130                 135                 140

Leu Glu Lys Gln His Ala Arg Asp Val Glu Phe Arg Lys Asp Leu Ile
145                 150                 155                 160

Glu Ser Thr Ile Asp Arg Gln Lys Arg Glu Val Asp Leu Glu Ala Lys
                165                 170                 175

Met Ala Lys Arg Glu Leu Asp Arg Glu Gly Gln Leu Ala Lys Glu Ala
            180                 185                 190

Leu Glu Arg Ser Arg Leu Ala Thr Asn Met Thr Glu Glu Ala Arg Arg
        195                 200                 205

Asp Gln Glu Arg Tyr Arg Gln Glu Gln Glu Ser Ile Ala Lys Gln Gln
    210                 215                 220

Glu Arg Glu Met Glu Lys Lys Thr Glu Ala Tyr Arg Lys Thr Ala Glu
225                 230                 235                 240

Ala Glu Ala Glu Lys Ile Arg Lys Glu Leu Glu Lys Gln His Ala Arg
                245                 250                 255

Asp Val Glu Phe Arg Lys Asp Leu Ile Glu Ser Thr Ile Asp Arg Gln
            260                 265                 270

Lys Arg Glu Val Asp Leu Glu Ala Lys Met Ala Lys Arg Glu Leu Asp
        275                 280                 285

Arg Glu Gly Gln Leu Ala Lys Glu Ala Leu Glu Arg Ser Arg Leu Ala
    290                 295                 300

Thr Asn Val Glu Val Asn Phe Asp Ser Ala Ala Gly His Thr Val Ser
305                 310                 315                 320

Gly Gly Thr Thr Val Ser Thr Ser Asp Lys Met Glu Ile Lys Arg Asn
                325                 330                 335
```

<210> SEQ ID NO 29
<211> LENGTH: 273
<212> TYPE: DNA
<213> ORGANISM: Artificial
<220> FEATURE:
<223> OTHER INFORMATION: Modified Tardigrade CAHS Protein (Mutant N CAHS Protein, No C Teminus or Linker Region) (DNA)

<400> SEQUENCE: 29

```
atgtcagggc gtaacgtgga gtcccatatg gagcgcaacg aaaaagtggt agtgaataac     60
tccggtcatg cggacgtgaa aaaacagcaa caacaggttg aacatacgga gttcacgcat    120
acagaagtaa aagccccgct catccaccca gcccctccga ttatttcgac tggcgccgcg    180
ggcttagcgg aggaaattgt gggccagggt tttactgcgt cagcagcgcg tatctcaggt    240
ggcactgccg aagtgcatct gcagccgtca taa                                 273
```

<210> SEQ ID NO 30
<211> LENGTH: 94
<212> TYPE: PRT
<213> ORGANISM: Artificial
<220> FEATURE:
<223> OTHER INFORMATION: Modified Tardigrade CAHS Protein (Mutant N CAHS Protein, No C Teminus or Linker Region) (Protein)

<400> SEQUENCE: 30

```
Met Gly Ser Ser Met Ser Gly Arg Asn Val Glu Ser His Met Glu Arg
  1               5                  10                  15

Asn Glu Lys Val Val Asn Asn Ser Gly His Ala Asp Val Lys Lys
             20                  25                  30

Gln Gln Gln Gln Val Glu His Thr Glu Phe Thr His Thr Glu Val Lys
         35                  40                  45

Ala Pro Leu Ile His Pro Ala Pro Pro Ile Ile Ser Thr Gly Ala Ala
     50                  55                  60

Gly Leu Ala Glu Glu Ile Val Gly Gln Gly Phe Thr Ala Ser Ala Ala
 65                 70                  75                  80

Arg Ile Ser Gly Gly Thr Ala Glu Val His Leu Gln Pro Ser
                 85                  90
```

<210> SEQ ID NO 31
<211> LENGTH: 684
<212> TYPE: DNA
<213> ORGANISM: Artificial
<220> FEATURE:
<223> OTHER INFORMATION: Modified Tardigrade CAHS Protein (Mutant FL-Proline CAHS Protein, Prolines Inserted) (DNA)

<400> SEQUENCE: 31

```
atgtcgggcc gtaacgtcga atctcacatg gaacgtaatg agaaggtggt ggtgaacaac     60
agcgggcacg ctgatgtcaa aaagcaacag cagcaggtag aacatacgga gtttacccat    120
actgaagtga agcccccatt aatccaccct gccccgccga ttattagcac gggtgctgcc    180
ggtttagcgg aggaaattgt gggacagggt tttacagcga gcgcagctcg tatcagtgga    240
ggtacggctg aagtccatct gcaaccaagc gcggcaatga cagaagaagc ccgccgtgat    300
caggagcgct atcgtcaaga acaggagtct attgcaaagc agcaagagcg cgagatggaa    360
aaaaagaccg aagcctaccg caaaaccgcc gaagcagaag ccgaaaagat tcgtaaggag    420
ctggaaaaac aacatgcccg tgatgtagaa ttccgtaaag atctgatcga gagcaccatt    480
gatcgtcaaa aacgcgaggt tgatctggaa gcaaagatgg ccaaacgtga actggatcgt    540
gaggggcagc ttgcaaagga ggcactggaa cgcagccgct agccacgaa cgtaccagtc    600
aatttcccga gtgccgctgg acacacggtt tcaggaggaa ccaccccatc gaccagtgac    660
aagatgccga tcaaacgtaa ctaa                                           684
```

<210> SEQ ID NO 32

-continued

```
<211> LENGTH: 231
<212> TYPE: PRT
<213> ORGANISM: Artificial
<220> FEATURE:
<223> OTHER INFORMATION: Modified Tardigrade CAHS Protein (Mutant
      FL-Proline CAHS Protein, Prolines Inserted) (Protein)

<400> SEQUENCE: 32

Met Gly Ser Ser Met Ser Gly Arg Asn Val Glu Ser His Met Glu Arg
1               5                   10                  15

Asn Glu Lys Val Val Asn Asn Ser Gly His Ala Asp Val Lys Lys
            20                  25                  30

Gln Gln Gln Gln Val Glu His Thr Glu Phe Thr His Thr Glu Val Lys
        35                  40                  45

Ala Pro Leu Ile His Pro Ala Pro Pro Ile Ile Ser Thr Gly Ala Ala
    50                  55                  60

Gly Leu Ala Glu Glu Ile Val Gly Gln Gly Phe Thr Ala Ser Ala Ala
65                  70                  75                  80

Arg Ile Ser Gly Gly Thr Ala Glu Val His Leu Gln Pro Ser Ala Ala
                85                  90                  95

Met Thr Glu Glu Ala Arg Arg Asp Gln Glu Arg Tyr Arg Gln Glu Gln
            100                 105                 110

Glu Ser Ile Ala Lys Gln Gln Glu Arg Glu Met Glu Lys Lys Thr Glu
        115                 120                 125

Ala Tyr Arg Lys Thr Ala Glu Ala Ala Glu Lys Ile Arg Lys Glu
    130                 135                 140

Leu Glu Lys Gln His Ala Arg Asp Val Glu Phe Arg Lys Asp Leu Ile
145                 150                 155                 160

Glu Ser Thr Ile Asp Arg Gln Lys Arg Glu Val Asp Leu Glu Ala Lys
                165                 170                 175

Met Ala Lys Arg Glu Leu Asp Arg Glu Gly Gln Leu Ala Lys Glu Ala
            180                 185                 190

Leu Glu Arg Ser Arg Leu Ala Thr Asn Val Pro Val Asn Phe Pro Ser
        195                 200                 205

Ala Ala Gly His Thr Val Ser Gly Gly Thr Thr Pro Ser Thr Ser Asp
    210                 215                 220

Lys Met Pro Ile Lys Arg Asn
225                 230
```